(12) United States Patent
Li et al.

(10) Patent No.: US 11,613,729 B2
(45) Date of Patent: Mar. 28, 2023

(54) CORTICAL SPHEROIDS AND METHODS OF MAKING THE SAME

(71) Applicant: The Florida State University Research Foundation, Inc., Tallahassee, FL (US)

(72) Inventors: Yan Li, Tallahassee, FL (US); Teng Ma, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 390 days.

(21) Appl. No.: 16/821,395

(22) Filed: Mar. 17, 2020

(65) Prior Publication Data
US 2020/0299642 A1 Sep. 24, 2020

Related U.S. Application Data

(60) Provisional application No. 62/821,807, filed on Mar. 21, 2019.

(51) Int. Cl.
C12N 5/079 (2010.01)

(52) U.S. Cl.
CPC ...... *C12N 5/0618* (2013.01); *C12N 2501/165* (2013.01); *C12N 2501/20* (2013.01); *C12N 2501/999* (2013.01); *C12N 2502/08* (2013.01); *C12N 2502/088* (2013.01); *C12N 2502/1352* (2013.01); *C12N 2502/28* (2013.01); *C12N 2513/00* (2013.01); *C12N 2533/80* (2013.01)

(58) Field of Classification Search
CPC .............. C12N 5/0618; C12N 2501/20; C12N 2501/999; C12N 2502/08; C12N 2502/088; C12N 2502/1352; C12N 2502/28; C12N 2513/00; C12N 2533/80
See application file for complete search history.

(56) References Cited

PUBLICATIONS

Song, Liqing. "Modelling 3-D brain-like tissues using human stem cell-derived vascular spheroids, cortical spheroids and microglia-like cells." (2018). Florida State University Dissertation. (Year: 2018).*
X. Yin, et al., Engineering stem cell organoids, Cell Stem Cell, 18 (2016) 25-38.
S.P. Pasca, The rise of three-dimensional human brain cultures, Nature, 553 (2018) 437-445.
E. Di Lullo, A.R. Kriegstein, The use of brain organoids to investigate neural development and disease, Nat Rev Neurosci, 18 (2017) 573-584.
F. Birey, et al., Assembly of functionally integrated human forebrain spheroids, Nature, 545 (2017) 54-59.

(Continued)

*Primary Examiner* — Kara D Johnson
(74) *Attorney, Agent, or Firm* — Eversheds Sutherland (US) LLP

(57) ABSTRACT

Improved hybrid neurovascular spheroids and methods for making the same are provided. In some embodiments of a method for making a hybrid neurovascular spheroid, the method includes i) propagating cortical cells to form a cortical spheroid; ii) propagating endothelial cells to form an endothelial spheroid; iii) propagating mesenchymal stem cells to form a mesenchymal cell culture; and iv) combining the cortical spheroid, endothelial spheroid, and mesenchymal spheroid under conditions to form the hybrid neurovascular spheroid.

13 Claims, 33 Drawing Sheets
Specification includes a Sequence Listing.

(56) References Cited

PUBLICATIONS

Y. Xiang, et al., Fusion of Regionally Specified hPSC-Derived Organoids Models Human Brain Development and Interneuron Migration, Cell Stem Cell, 21 (2017) 383-398.

J.A. Bagley, et al., Fused cerebral organoids model interactions between brain regions, Nat Methods, 14 (2017) 743-751.

P.A. Fleming, et al., Fusion of uniluminal vascular spheroids: a model for assembly of blood vessels, Dev Dyn, 239 (2010) 398-406.

L. Moldovan, et al., iPSC-Derived Vascular Cell Spheroids as Building Blocks for Scaffold-Free Biofabrication, Biotechnol J, (2017). doi: 10.1002/biot.201700444.

T. Takebe, et al., Vascularized and complex organ buds from diverse tissues via mesenchymal cell-driven condensation. Cell Stem Cell, 16 (2015) 556-565.

A.D. Wong, et al., The blood-brain barrier: an engineering perspective, Front Neuroeng, 6 (2013) 7.

A. Appelt-Menzel, et al., Establishment of a Human Blood-Brain Barrier Co-culture Model Mimicking the Neurovascular Unit Using Induced Pluri- and Multipotent Stem Cells, Stem Cell Reports, 8 (2017) 894-906.

S. Sart, et al., Three-dimensional aggregates of mesenchymal stem cells: cellular mechanisms, biological properties, and applications, Tissue Eng Part B Reviews, 20 (2014) 365-380.

L. Song, et al., Neural differentiation of spheroids derived from human induced pluripotent stem cells-mesenchymal stem cells co-culture, Tissue Eng Part A, 24 (2018) 915-929.

A.C. Tsai, et al., Compaction, fusion, and functional activation of three-dimensional human mesenchymal stem cell aggregate, Tissue Eng Part A, 21 (2015) 1705-1719.

M. Campisi, et al., 3D self-organized microvascular model of the human blood-brain barrier with endothelial cells, pericytesand astrocytes, Biomaterials, 180 (2018) 117-129.

L.M. Acevedo, et al., hESC Differentiation toward an Autonomic Neuronal Cell Fate Depends on Distinct Cues from the Co-Patterning Vasculature, Stem Cell Reports, 4 (2015) 1075-1088.

W.X. Gao, et al., Effects of mesenchymal stem cells from human induced pluripotent stem cells on differentiation, maturation, and function of dendritic cells, Stem Cell Res Ther, 8 (2017) 48.

A.A. Mansour, et al., An in vivo model of functional and vascularized human brain organoids, Nat Biotechnol, 36 (2018) 432-441.

M.T. Pham, et al., Generation of human vascularized brain organoids, Neuroreport, 29 (2018) 588-593.

\* cited by examiner

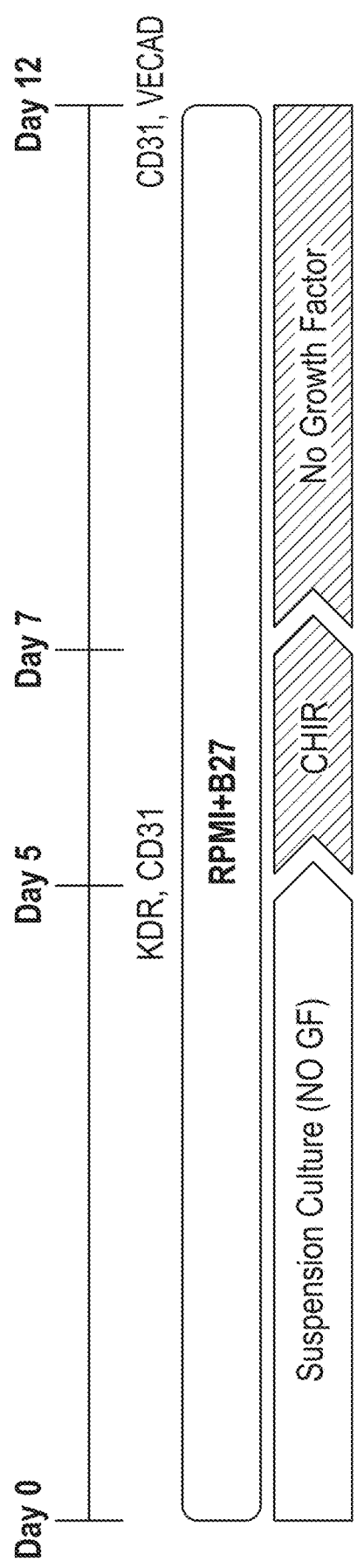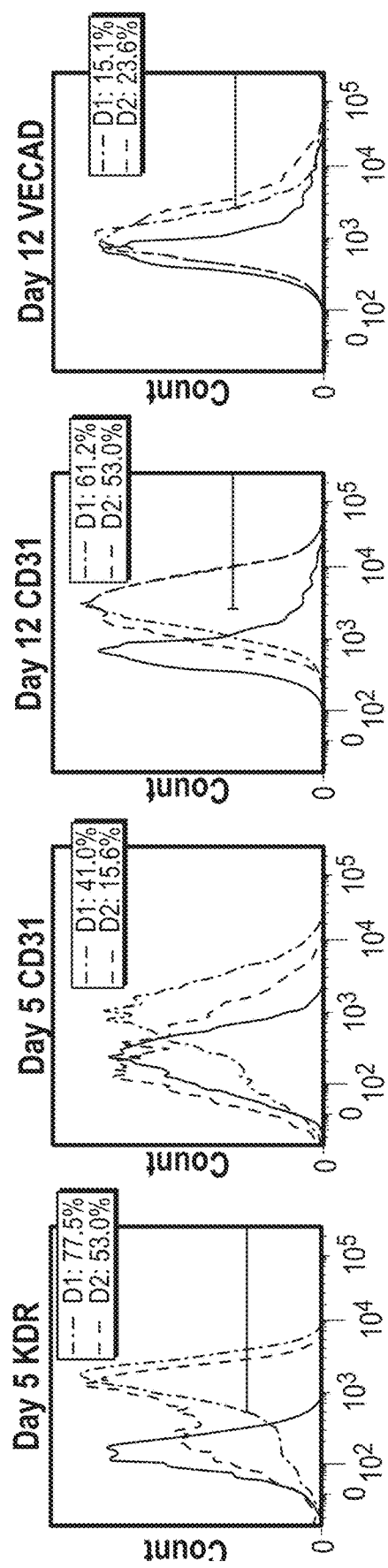
FIG. 1A
FIG. 1B

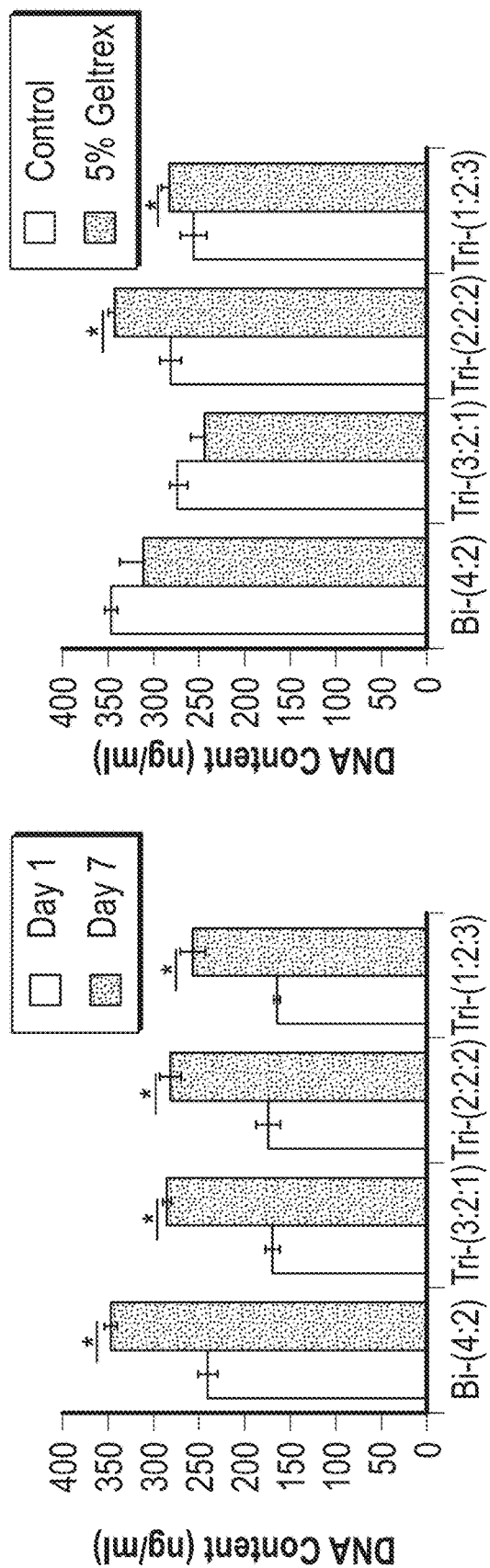
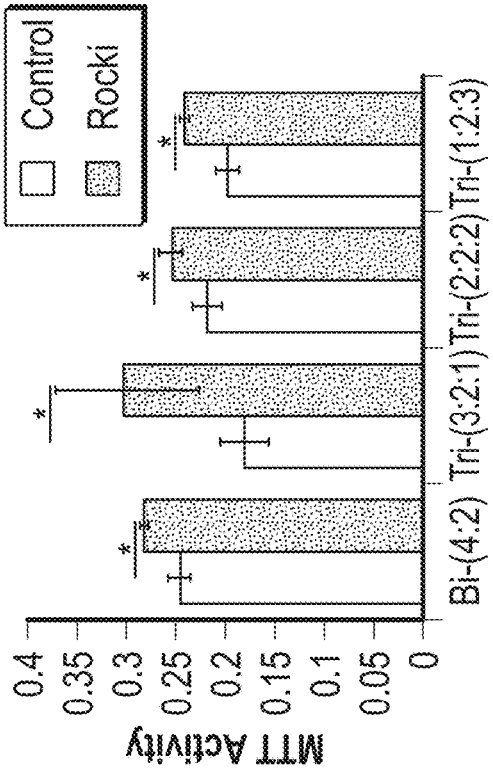
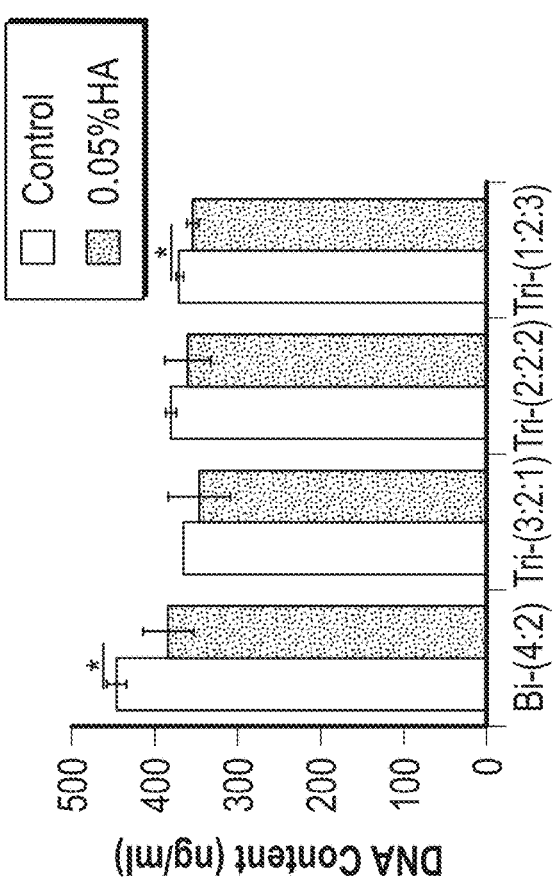
FIG. 11A, FIG. 11B, FIG. 11C, FIG. 11D

CORTICAL SPHEROIDS AND METHODS OF MAKING THE SAME

CROSS-REFERENCE TO RELATED APPLICATIONS

This application claims priority to and benefit of U.S. Provisional Application No. 62/821,807 filed Mar. 21, 2019, which is incorporated herein by reference.

STATEMENT REGARDING FEDERALLY SPONSORED RESEARCH

This invention was made with government support under Grant No. R03EB020770 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 16, 2020, is named 19585-0393_SL.txt and is 4,806 bytes in size.

BACKGROUND

Brain organoids derived from human induced pluripotent stem cells (hiPSCs) have emerged as powerful model systems for neurological disease modeling, drug screening, and for studying Zika virus infections [1-5], which affect over one billion people globally [6], as well as microcephaly [3], and lissencephaly [63]. However, the lack of interactions with other cell types such as endothelial cells in current brain organoids model limits their applications [5, 9]. As neurological diseases, such as blood-brain barrier (BBB) breakdown and dysfunction in Alzheimer's and stroke, involve multiple cell types, in vitro models such as brain organoids must include relevant cell types to reconstruct cellular microenvironment [13]. As the vascular system is an essential component of brain tissue, incorporating neural-vascular interactions in forebrain organoids is an important step in developing brain organoids in vitro. To date, the actual vascularization was only achieved in vivo [18, 19, 84]. In vitro vascularization needs accurate design of ECM amounts and the structure (insoluble) and the soluble secreted factors. Whole brain organoids derived from hiPSCs in Matrigel with isogenic ECs or coated day 34 spheroids with ECs have been used to achieve in vitro and in vivo vascularization [85]. In another study from Mansour et al. (2018), vascularized brain organoids in vivo show the integration of microglia and functional neuronal networks and blood vessels [84]. All these studies indicate that neural-vascular interactions are indispensable for modeling neurological diseases and screening drugs that require 3-D brain tissue structure [64]. This is particularly true for the use of diseased hiPSC lines such as in Alzheimer's disease [31]. Alzheimer's-patient derived cortical organoids containing vascular cells would be important to recapitulate a neurodegenerative microenvironment and investigate its response to potential drug treatments.

However, generating brain-region specific organoids with defined structure and function remains a critical challenge because the heterotypic cell-cell interactions to mimic the human brain have not yet been fully understood [7-9]. Recently, fusion of human forebrain spheroids of different regions (e.g., human dorsal spheroids with ventral spheroids) has been investigated to model interneuron migration and the interactions of different neuronal subtypes [10-12]. However, the interactions of neuronal cells with other cell types, such as endothelial cells, have not been fully studied in brain organoids [5].

Cerebral organoids derived from induced pluripotent stem cells (iPSCs) provide novel tools for recapitulating the cytoarchitecture of the human brain and for studying biological mechanisms of neurological disorders. However, these cerebral organoids typically do not allow for the observation of heterotypic interactions of neurovascular units, composed of neurons, pericytes, astrocytes, and brain microvascular endothelial cells, in brain-like tissues.

Accordingly, improved cerebral organoids and methods of making the same are needed.

BRIEF SUMMARY

Improved hybrid neurovascular spheroids and methods for making the same are provided. In one aspect, a method is provided for making a hybrid neurovascular spheroid, wherein the method includes i) propagating cortical cells to form a cortical spheroid; ii) propagating endothelial cells to form an endothelial spheroid; iii) propagating mesenchymal stem cells to form a mesenchymal cell culture; and iv) combining the cortical spheroid, endothelial spheroid, and mesenchymal spheroid under conditions to form the hybrid neurovascular spheroid.

In some embodiments, at least a portion of the mesenchymal cell culture is combined with the cortical spheroid first, to form a mesenchymal cell-cortical spheroid which is then combined with the endothelial spheroid to form the hybrid neurovascular spheroid. In some other embodiments, at least a portion of the mesenchymal cell culture is combined with the endothelial spheroid first, to form a mesenchymal cell-endothelial spheroid which is then combined with the cortical spheroid to form the hybrid neurovascular spheroid.

In some embodiments, the cortical cells are human iPSC-derived cortical neural progenitor cells (iNPC), cortical cells are pericytes, astrocytes, or microglia. In some embodiments, the endothelial cells are human endothelial cells (iEC) and/or the mesenchymal stem cells are human mensenchymal stem cells (hMSC).

In some embodiments, the one or more of the cortical cells, endothelial cells, and mesenchymal stem cells are propagated in a hydrogel comprising Geltrex, hyaluronic acid (HA), or any combination thereof. In some embodiments, the method further includes treating one or more of the spheroids with a CXCR4 antagonist, including AMD3100.

In another aspect, a hybrid neurovascular spheroid is provided that includes cortical cells, endothelial cells, and mesenchymal stem cells. In some embodiments, the hybrid neurovascular spheroid displays upregulated secretion levels of one or more cytokines VEGF-A, PGE2, and TBF-β1 relative to a comparative hybrid neurovascular spheroid prepared by directly mixing cultures of cortical cells, endothelial cells, and mesenchymal stem cells.

In some embodiments, the hybrid neurovascular spheroid displays increased expression of one or more of TBR1, Nkx2.1, matrix remodeling, MMP2, MMP3, Notch-1, GLUT-1, CD31, or ZO-1 genes relative to a comparative hybrid neurovascular spheroid prepared by directly mixing cultures of cortical cells, endothelial cells, and mesenchymal stem cells.

In some embodiments, the hybrid neurovascular spheroid has a ratio based on initial seeded cell numbers of the cortical cells to the endothelial cells to the mesenchymal stem cells wherein the ratio is from about 4:2:0 to about 1:2:3.

BRIEF DESCRIPTION OF THE DRAWINGS

FIGS. 1A-1D depict the endothelial differentiation from hiPSCs in suspension to generate iEC spheroids.

FIGS. 11A-11D depict the metabolic activity and DNA content of hybrid spheroids in suspension.

DETAILED DESCRIPTION

Figure 1C:
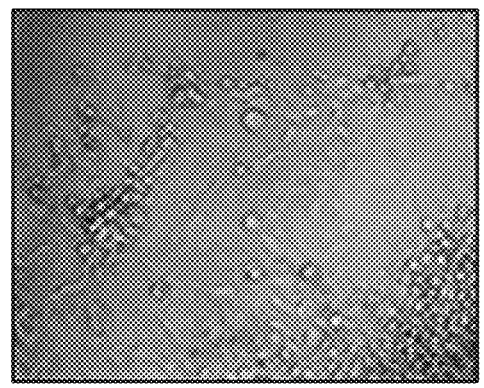

Hybrid neurovascular spheroids are provided that includes cortical cells, endothelial cells, and mesenchymal stem cells. The spheroid, or 3-D cell culture, is a fusion of aggregates of each cell type. That is, an aggregate of cortical cells, and an aggregate of endothelial cells, and an aggregate of mesenchymal stem cells, wherein the aggregates are fused into direct contact in a 3-D architecture. This spheroid structure is distinct from a 3-D culture in which the different cell types are mixed together before forming the 3-D architecture.

Neural-vascular interactions, known as neural-vascular units (NVU), play an important role in brain structure and function [13]. It is believed that organ-specific endothelial cells secrete a unique set of growth factors that regulate tissue morphogenesis into desired tissue types [14]. Vascular cells can form spheroids to assemble blood vessels or as building blocks for scaffold-free tissue fabrication [15, 16]. In vitro vascularization of organoids has been attempted for cardiac organoids, showing enhanced cardiac cell function [17]. In vivo vascularization of organoids was realized for iPSC-derived organ buds, in which the mixed iPSC-derived progenitors and endothelial cells efficiently self-organized into functional and vascularized liver or kidney in vivo respectively [18, 19]. In particular, the blood-brain barrier (BBB) is involved in various neurological diseases development, drug administration and nutrient transport [13, 20]. Functional BBB models require the interaction of brain microvascular endothelial cells (ECs), astrocytes, neurons, and pericytes, which can be realized using hiPSC-derived cells [21-24].

Mesenchymal stem cell (MSC)-driven condensation has been observed in organ buds formation based on iPSC-derived cells for multiple tissue types including kidney, intestine, brain, and heart etc., in the presence of MSCs [19]. Although it remains unclear if MSC-driven condensation is due to adhesion molecules expression or cytoskeleton reorganization, the MSCs support organoid formation from multiple aspects. MSCs reside in virtually all adult tissues including brain and the vicinity of the capillaries, and at least at a subset of MSCs ($CD146^+CD34^-$) can function as pericytes that are closely associated with vasculature [25-27]. In the context of brain organoids, MSC secretome are a potent source of trophic factors that are modulators of neurogenic niche and promote angiogenesis and neural differentiation through trophic effects (e.g., fibroblast growth factor (FGF)-2, vascular endothelial growth factor (VEGF), brain-derived neurotrophic factor etc.). MSCs also secrete anti-apoptotic and anti-inflammatory factors, e.g., Prostaglandin E2 (PGE2), and ECM proteins [28]. MSCs displayed higher homing ability to injury sites for neural protection, due to the increased expression of CXCR-4 [29]. Thus, without intending to be bound by any particular theory, it is believed that the incorporation of ECs and MSCs enables the formation of a pro-neurogenic niche that promotes angiogenesis, neo-brain tissue patterning, and maturation.

Previous studies have assembled hiPSC-derived neural progenitor cells (iNPCs) and human bone marrow MSCs in spheroid culture, showing that MSCs promote dorsal cortical spheroid formation [30]. The derivation of cortical spheroids or organoids was also achieved in a suspension bioreactor and from Alzheimer's patient specific hiPSCs [31-33].

However, without intending to be bound by any particular theory, it is believed that vascularization of cortical organoids in vitro through tri-culture of iNPCs, hiPSC-derived ECs, and human MSCs, may allow for the investigation of heterotypic neural-vascular-mesenchymal interactions.

Most previous methods directly mixed endothelial cells with other cell types for 3-D co-culture systems [17, 19, 64]. Advantageously, unlike direct mixing methods, the spheroid fusion methods described herein (1) avoid cell dissociation and re-association processes, which could lose many cells; and (2) the hybrid spheroid structure can be pre-controlled with special compartment arrangements.

The spheroid fusion method has been used for assembly of dorsal and ventral forebrain spheroids to study interneuron migration and the assembly of iPSC-derived endothelial progenitor spheroids and smooth muscle progenitor spheroids [10, 16]. Fusion of spheroids of different cell types is most likely driven by minimization of interfacial free energy and cellular thermodynamics, differential cellular adhesions (e.g., E-cadherin expression), or cortical tension redistribution [28, 65, 66]. Without intending to be bound by any particular theory, it is believed that the fusion kinetics is affected by ROCK inhibitor, ECMs in the medium, and the mixing sequence. Without intending to be bound by any particular theory, it is believed that the addition of high concentration of ROCKi Y-27632 during the initial aggregation delayed the fusion process, indicating that cortical tension regulates spheroid fusion process, and that actomyosin may play a key role in spheroid fusion [47, 67]. Without intending to be bound by any particular theory, it is believed that the presence of GELTREX™, a soluble form of basement membrane, (Life Technologies Corporation) (hereinafter "Geltrex") and HA, an ECM component in the brain, at an appropriate concentration promotes spheroid fusion.

Without intending to be bound by any particular theory, it is believed that, since MSCs condense into the center of the hybrid spheroids, adding MSCs to iNPC spheroids before iEC spheroid fusion (iNPC-MSC-iEC) would constrict MSCs as the iNPC spheroid core. Accordingly, in some embodiments, the present disclosure includes iNPC spheroid and iEC spheroid fusion in the presence of MSCs (iNPC-iEC-MSC).

In some embodiments, assembly of vascular spheroids and cortical spheroids as disclosed herein may enhance the glucose transporter, GLUT-1 (specifically expressed in endothelial cells in brain [13]), and a polarized efflux transporter BCBP. In some embodiments, the tight junction protein ZO-1 may be promoted in the tri-culture, indicating that neurovascular co-patterning promotes the specification of iECs toward brain microvascular cells.

Human iPSC-derived 2-D co-culture system of multiple cell types (i.e., neurons, astrocytes, pericytes and brain microvascular endothelial cells) has been recently used to mimic BBB function with higher trans-endothelial electrical resistance (TEER) properties and study drug permeability in vitro [21-24]. Neural-vascular interactions result in the special structure and function of BBB. However, the 3-D BBB models have not been well established due to the complex BBB features and the difficulty of forming micro-vessel structures in 3-D. Some studies use hollow fiber systems with perfusion culture or artificially create microchannels for 3-D vascularization [20]. Although this system is not yet an accurate and perfusable 3-D BBB model, the system recapitulates the anatomical features of the BBB using human stem cells. The inclusion and characterization of additional cell types (e.g., astrocytes), more complex 3-D capillary network (novel biomaterials design), and perfusion flow (use bioreactors or microfluidics) may be explored in the future [68].

Without intending to be bound by any particular theory, it is believed that neural-vascular interactions may also impact brain tissue patterning. In some embodiments, hybrid spheroids may exhibit elevated β-tubulin III and CD31 expression, as well as higher TBR1 and Nkx2.1 gene expression in tri-culture (in particular the 1:2:3 group). In addition, it is believed that the "inside-out" development of the cortical superficial and deep layers in the forebrain is faster for the tri-(1:2:3) group compared to other groups. It has been reported that the neural differentiation of hPSCs requires the direct association with vascular cells [69] as well as hMSCs, possibly through MAPK and PI3K-Act signaling (involved FGF-2) [70]. In some embodiments, the tri-culture system described herein may promote the expression of Notch-1, the key protein in Notch signaling which is responsible for cell-cell contact interactions involved ECs [71, 72]. In addition, activation of Notch signaling can promote the neural stem cell self-renewal, glial cell differentiation, and neuron regeneration [73, 74]. Without intending to be bound by any particular theory, it is believed that the hybrid spheroids described herein may exhibit direct contact among iNPCs, iECs, and hMSCs at a given ratio, which may accelerate development of 3-D cortical tissue structure containing vascular cells to model human brain development.

The interactions of hMSCs and iNPC have been discussed in [30]. Without intending to be bound by any particular theory, it is believed that the presence of MSCs in addition to iECs was found to enrich ECM localization and affect matrix remodeling. As brain ECM has little fibril ECMs such as collagens [20], the expression of collagen IV in hybrid spheroids was mainly attributed to MSCs. Without intending to be bound by any particular theory, it is believed that the elevated MMP-2 and MMP-3 expression indicates the active matrix remodeling, which is required for maintaining neural stem cells [62]. It has been found that the formation of hMSC aggregates upregulates several types of MMPs (MMP-2, -9, and -1/13) [75], which were reported to enhance neuronal differentiation through NF-κB signaling [76]. Without intending to be bound by any particular theory, it is believed that ECM remodeling may also be an important contributing factor involved in the migration and invasion of the cells. In some embodiments, the hybrid spheroid, the immobilized hMSCs after CXCR4 (receptor for CXCL12/stromal-derived factor-1 chemokine) inhibition reveals the migration ability of hMSCs within the fused spheroids.

Secretion of cytokines and neurotrophin is a critical function of hMSCs, which can enhance neurogenesis of hiPSCs [77]. The influence of TGF-β1 and PGE2 secreted by MSCs on hiPSC-neural differentiation is known [30]. The upregulated TGF-β1 and PGE2 secretion by MSCs promotes Nestin and β-tubulin III expression. Without intending to be bound by any particular theory, it is believed that the main source of VEGF-A is hMSCs, although vascular cells also contribute to VEGF-A secretion. Previous studies have suggested that brain vascular ECs promote neural cell functionality, such as synaptic activities, via the modulation of VEGF signaling and that the VEGF receptors were activated by neural cell-secreted nitric oxide [78, 79]. Without intending to be bound by any particular theory, it is believed that iECs may be a minor source of VEGF-A (as shown in Bi-(4:2) group) in hybrid spheroids of the present disclosure as they are not mature enough compared to human bone marrow MSCs. The elevated VEGF-A in tri-culture (in particular the 1:2:3 group) regulated by Notch signaling is a result of close cell-cell contacts of neural-vascular-mesenchymal cells through autocrine, paracrine, and juxtacrine interactions [80, 81].

Without intending to be bound by any particular theory, it is believed that the cellular ratio indicates that tri-(1:2:3) better promotes neural-vascular interactions than the other groups, indicated by higher cytokine secretion, neural patterning marker expression, BBB-related gene expression, and the cortical layer separation. The brain composition showed a 1:3 neuron-to-astrocyte ratio [22], indicating the importance of accessory cells on neural function. In some embodiments, endothelial cell apoptosis may exist due to upregulated caspase3/7 expression and altered mitochondria bioenergetics on 3-D MSC aggregation due to compaction [82]. An alternative is the use of iPSC-derived MSC (iMSCs) in the tri-culture system as reported by Gao et al. [83].

In some embodiments of the present disclosure, hiPSC-derived vascular spheroids and hiPSC-derived neural cortical spheroids are assembled in the presence of hMSCs to study neurovascular interactions. Without intending to be bound by any particular theory, it is believed that the presence of hMSCs promotes cortical neural differentiation, layer separation, cytokine secretion, and cell-cell communication. Without intending to be bound by any particular theory, it is believed that the presence of iECs provides the BBB-related properties inside the cortical spheroids or organoids. In some embodiments, hybrid spheroids may exhibit elevated Notch signaling, matrix remodeling proteins, and secretion of VEGF-A. Without intending to be bound by any particular theory, it is believed that this may contribute to the accelerated cortical tissue development.

In some embodiments of a method for making a hybrid neurovascular spheroid, the method includes i) propagating cortical cells to form a cortical spheroid; ii) propagating endothelial cells to form an endothelial spheroid; iii) propagating mesenchymal stem cells to form a mesenchymal cell culture; and iv) combining the cortical spheroid, endothelial spheroid, and mesenchymal spheroid under conditions to form the hybrid neurovascular spheroid.

In some embodiments, the step of combining the cortical spheroid, endothelial spheroid, and mesenchymal spheroid under conditions to form a fused spheroid includes i) combining at least a portion of the mesenchymal cell culture with the cortical spheroid to form a mesenchymal cell-cortical spheroid; and ii) combining the mesenchymal cell-cortical spheroid with the endothelial spheroid to form the hybrid neurovascular spheroid.

In some embodiments, the step of combining the cortical spheroid, endothelial spheroid, and mesenchymal spheroid under conditions to form a fused spheroid includes i) combining at least a portion of the mesenchymal cell culture with the endothelial spheroid to form a mesenchymal cell-endothelial spheroid; and ii) combining the mesenchymal cell-endothelial spheroid with the cortical spheroid to form the hybrid neurovascular spheroid.

In some embodiments, the cortical cells are human iPSC-derived cortical neural progenitor cells (iNPC). In some embodiments, the cortical cells are pericytes, astrocytes, or microglia.

In some embodiments, the endothelial cells are human endothelial cells (iEC). In some embodiments, the mesenchymal stem cells are human mensenchymal stem cells (hMSC).

In some embodiments, the ratio based on initial seeded cell numbers of the cortical cells to the endothelial cells to the mesenchymal stem cells is from about 4:2:0 to about 1:2:3.

In some embodiments, the cortical cells, endothelial cells, and mesenchymal stem cells are propagated in separate low-attachment well plates or in other suitable vessels.

In some embodiments, the one or more of the cortical cells, endothelial cells, and mesenchymal stem cells are propagated in a hydrogel comprising Geltrex, hyaluronic acid (HA), or any combination thereof. In some embodiments, the one or more cortical cells, endothelial cells, and mesenchymal stem cells are propagated in a hydrogel comprising at least about 5 wt. % Geltrex and 0.025 wt. % HA.

In some embodiments, the method further includes treating one or more of the spheroids with a CXCR4 antagonist. In some embodiments, the CXCR4 antagonist is AMD3100.

In some embodiments, a hybrid neurovascular spheroid is provided that includes cortical cells, endothelial cells, and mesenchymal stem cells.

In some embodiments, the hybrid neurovascular spheroid displays upregulated secretion levels of one or more cytokines VEGF-A, PGE2, and TBF-β1 relative to a comparative hybrid neurovascular spheroid prepared by directly mixing cultures of cortical cells, endothelial cells, and mesenchymal stem cells.

In some embodiments, the hybrid neurovascular spheroid displays increased expression of one or more of TBR1, Nkx2.1, matrix remodeling, MMP2, MMP3, Notch-1, GLUT-1, CD31, or ZO-1 genes relative to a comparative hybrid neurovascular spheroid prepared by directly mixing cultures of cortical cells, endothelial cells, and mesenchymal stem cells.

In some embodiments, the cortical cells are human iPSC-derived cortical neural progenitor cells. In some embodiments, the endothelial cells are human endothelial cells. In some embodiments, the mesenchymal stem cells are human mensenchymal stem cells (hMSC).

In some embodiments, the hybrid neurovascular spheroid has a ratio based on initial seeded cell numbers of the cortical cells to the endothelial cells to the mesenchymal stem cells wherein the ratio is from about 4:2:0 to about 1:2:3.

In some embodiments, the hybrid neurovascular spheroid includes one or more of cortical cells, endothelial cells, and/or mesenchymal stem cells that are propagated in a hydrogel. The hydrogel may include Geltrex, hyaluronic acid, or a combination thereof.

The hybrid neurovascular spheroids made by the methods described herein have a variety of applications. For example, the spheroids may be used as a research tool, including as a research model for testing pharmaceuticals or other substances' effects on healthy or diseased neurovascular tissue. Furthermore, the spheroids have several applications in the field of tissue engineering, including the formation of tissue for medical treatment.

The spheroids and methods can be further understood with the following non-limiting examples.

EXAMPLES

In each of the examples described below, the human iPSK3 cells used were derived from human foreskin fibroblasts transfected with plasmid DNA encoding reprogramming factors OCT4, NANOG, SOX2 and LIN28 (kindly provided by Dr. Stephen Duncan, Medical College of Wisconsin, and Dr. David Gilbert, Department of Biological Sciences of Florida State University) [34, 35]. The human iPSK3 cells were maintained in mTeSR serum-free medium (StemCell Technologies, Inc., Vancouver, Canada) on 6-well plates coated with growth factor reduced Geltrex (Life Technologies). The cells were passaged by Accutase dissociation every 5-6 days and seeded at $1\times10^6$ cells per well of 6-well plate in the presence of 10 μM Y27632 (Sigma) for the first 24 hours [36-38].

Each experiment was carried out at least three times (using different batches of cells) with triplicate samples (in some cases spheroids were pooled from more than 12 wells) in each experiment. The representative experiments were presented and the results were expressed as [mean±standard deviation]. To assess the statistical significance, one-way ANOVA followed by Fisher's LSD post hoc tests were performed. A p-value <0.05 was considered statistically significant.

Example 1: hMSC Culture Formation and iEC and iNPC Spheroid Formation

To generate a human MSC (hMSC) culture, standardized frozen hMSCs from multiple donors were obtained from the Tulane Center for Gene Therapy and cultured as previously described [39, 40]. The hMSCs were isolated from the bone marrow of healthy donors ranging in age from 19 to 49 years based on plastic adherence, negative for CD34, CD45, CD117 (all less than 2%) and positive for CD29, CD44, CD49c, CD90, CD105, and CD147 markers (all greater than 95%), and possessed tri-lineage differentiation potential upon induction in vitro [41, 42]. hMSCs were expanded at a density of $1.7\times10^3$ cells/cm$^2$ using MEM (Invitrogen) medium supplemented with 10% fetal bovine serum (FBS) and 1% penicillin/streptomycin. At approximately 80% confluence, adherent cells were harvested with 0.25% trypsin-EDTA (Sigma-Aldrich) and further propagated.

Figure 1D:
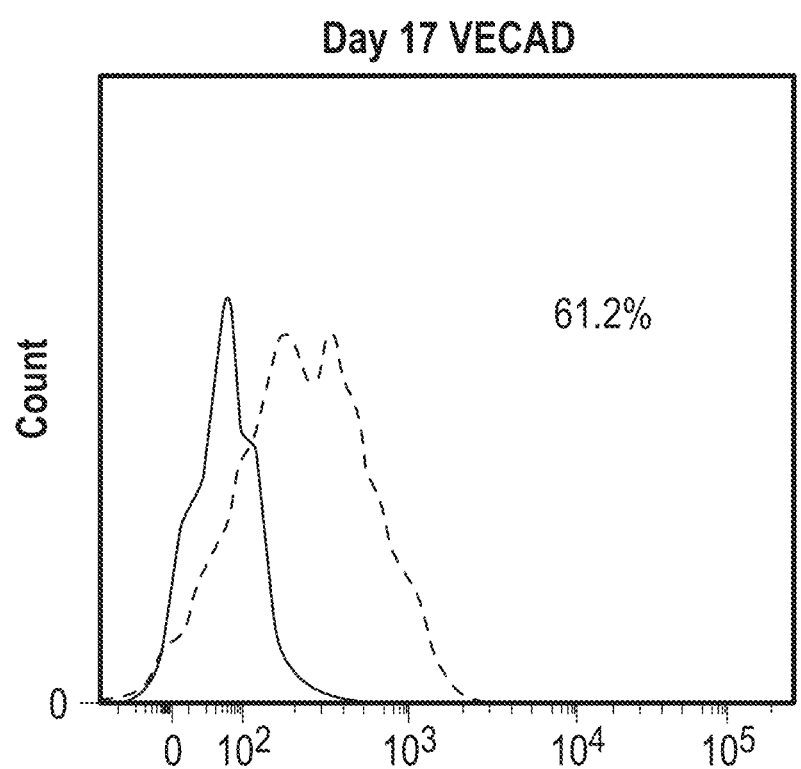

To generate an endothelial cell spheroid (iEC), undifferentiated iPSK3 cells were seeded in U-bottom ultra-low-attachment (ULA) 96-well plates (Corning Inc.) at $1\times10^4$ per well (unless otherwise noted) in differentiation medium composed of RPMI plus 2% B27 (Life Technologies) for 3 days. Y27632 (10 μM) was added during the seeding and removed after 24 h. Then Wnt activator CHIR99021 (10 μM, StemCell Technologies Inc.) was added to the culture medium for 5 days followed by another 6 days in medium without CHIR99021 [43-45]. iEC aggregates (day 14) were characterized or transferred to the wells containing iNPC spheroids. The iEC spheroids expressed endothelial markers CD31 and VE-cadherin, as illustrated in FIGS. 1A-1B. Specifically, FIG. 1A is a schematic illustration of endothelial differentiation protocol. FIG. 1B shows vascular markers, CD31 and VE-cadherin (VECAD), expression was quantified by flow cytometry. Solid line: negative control; dashed lines: marker of interest from two differentiations. Day 11 vascular spheroids were re-plated for one day and immunocytochemistry was performed for vascular markers (not shown). Day 14 vascular spheroids were harvested and prepared for histology sections (not shown). Haemotoxylin and Eosin (H&E) staining and CD31 staining was performed (not shown). Vascular network formation was observed for day 14 iEC spheroids re-plated on 1:1 Geltrex-coated surface in endothelial medium and cultured for 7 days (FIG. 1C). Scale bar: 100 μm. Briefly, 24-well plates were coated with 200 μL/well 1:1 diluted Geltrex for more than 30 min. The cells were plated at $5\times10^5$ cells on Geltrex-coated plates in 500 μL EGM-2 medium (Lonza, for endothelial cells) and incubated at 37° C. in 5% $CO_2$ for 7 days. Cell morphology was photographed by a phase-contrast microscope (not shown). VE-cadherin staining of iEC after 30 days of differentiation was performed (not shown). VE-cadherin (VECAD), expression in day 17 iECs was quantified by flow cytometry (FIG. 1D).

Figure 2A:
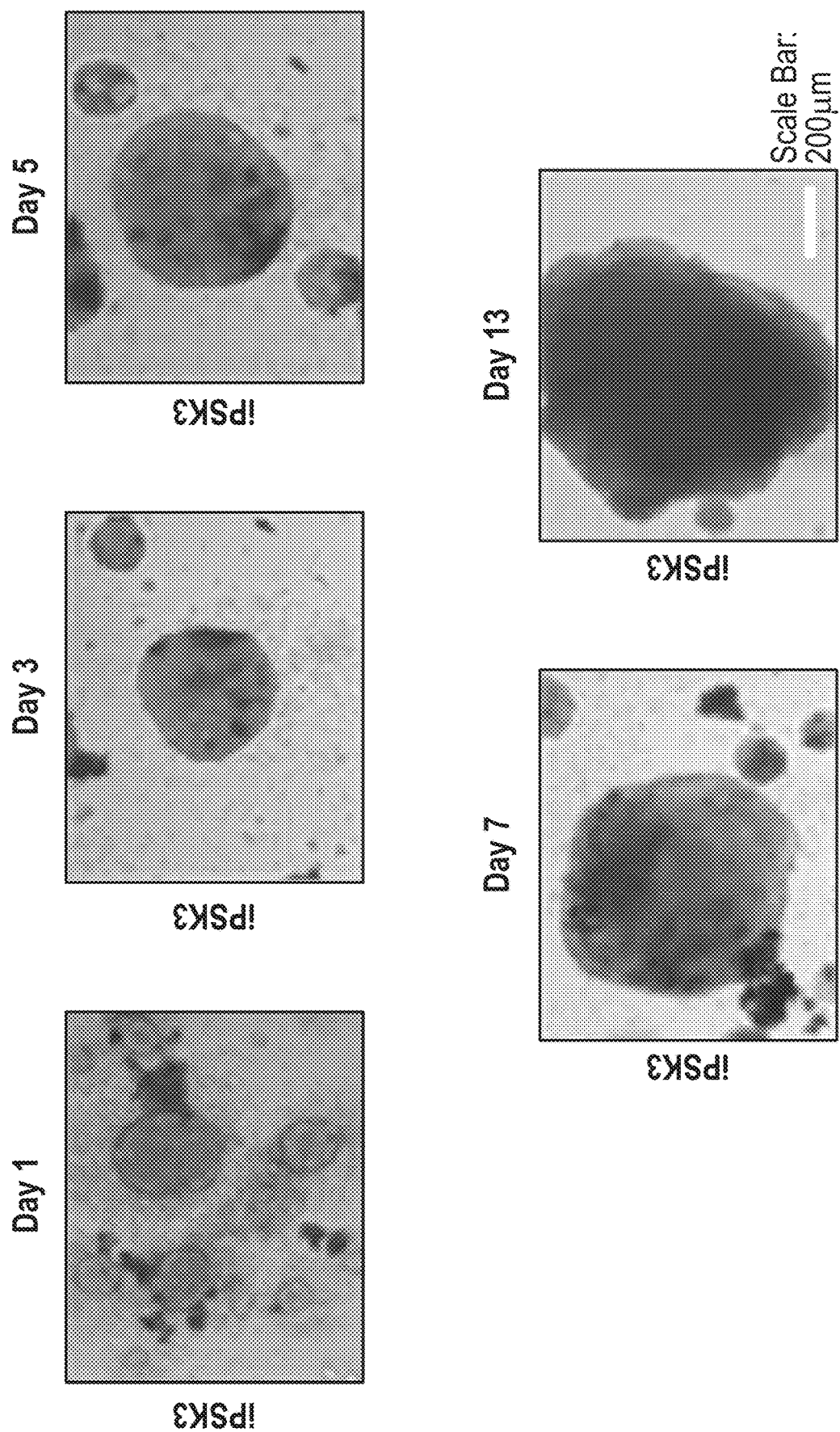
FIGS. 2A-2C depict the characterization of neural differentiation from hiPSCs in suspension.
Figure 2B:
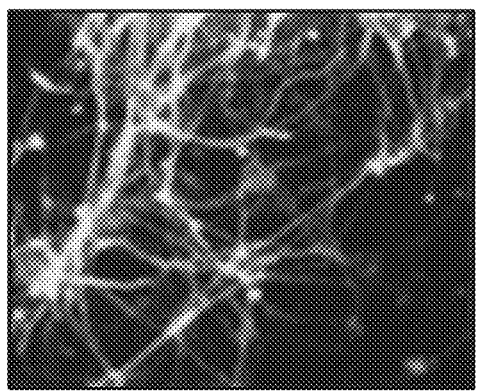
Figure 2B:
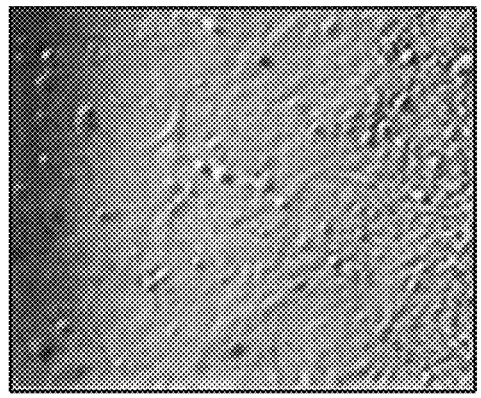
Figure 2C:
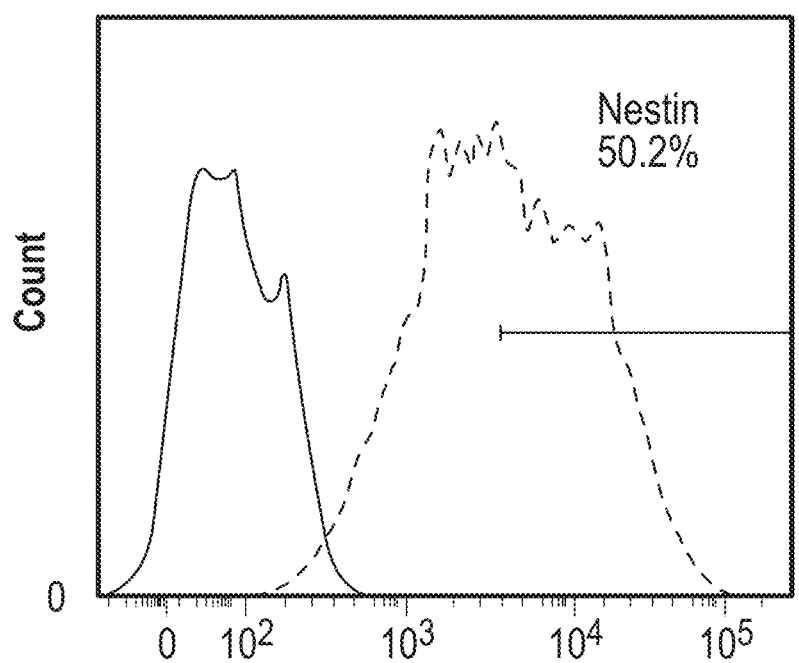
Figure 2C:
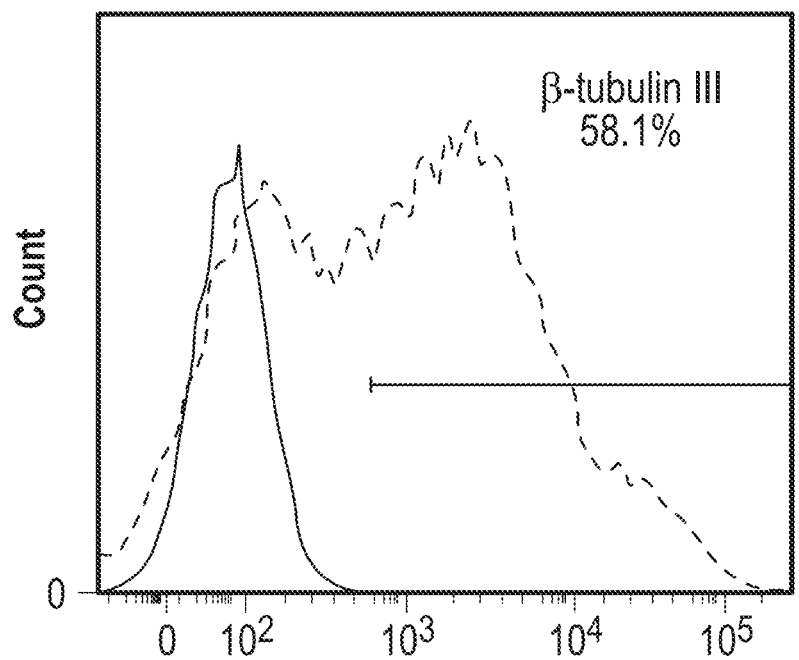

To generate a cortical iNPC spheroid, undifferentiated iPSK3 cells ($0.5\text{-}2\times10^4$ cells) were seeded into U-bottom ULA 96-well plates in neural differentiation medium composed of DMEM/F-12 plus 2% B27 in the presence of Y27632 (10 μM). The aggregates were treated with 10 μM SB431542 (Sigma) and 100 nM LDN193189 (Sigma) for 7 days [31]. At day 7, the spheroids were treated with retinoic acid (RA) (2 μM, Sigma) and FGF-2 (25 ng/mL, Life Technologies) and grown in neural medium for another 7 days [37]. For maturation, cortical spheroids were maintained in neural differentiation medium without growth factors for additional 7-38 days. The NPC spheroids expressed various neuronal markers such as Nestin, TBR1 and β-tubulin III, as shown in FIGS. 2A-2B [33]. Specifically, FIG. 2A shows phase contrast images of iNPC spheroids morphology over 13 days. Scale bar: 200 μm. Confocal images of cortical neuron marker TBR1 and hindbrain marker HOXB4 were taken for day 14 iNPC spheroids (not shown). Neural progenitor marker expression of Nestin and TBR1 of re-plated day 14 iNPC spheroids was observed (not shown). FIG. 2B shows neurite outgrowth and axon extension indicated by β-tubulin III expression and phase contrast images of neurons after replating. Scale bar: 100 μm. Different phenotypic marker expression on day 28 was observed using Glutamate/Tau and Synapsin-1 (SYN-1)/β-tubulin III, related to neurogenesis. (not shown). FIG. 2C shows flow cytometry analysis of Nestin and β-tubulin III (day 20). Solid line: negative control; dashed line: marker of interest.

Figure 3:
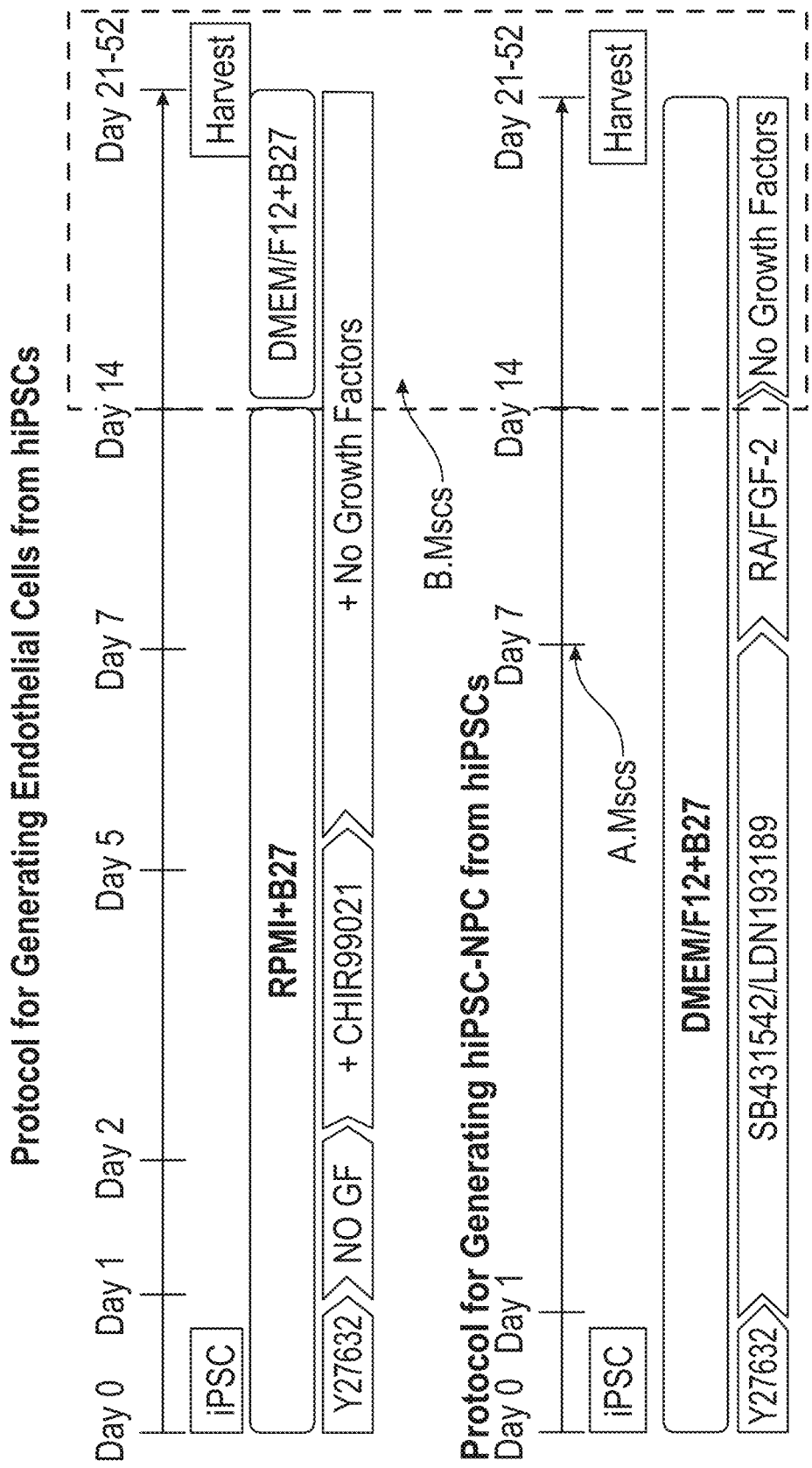
FIG. 3 depicts methods to form hybrid spheroids according to embodiments of the present disclosure.

Next, using these individual iNPC, MSC, and iEC spheroids, hybrid spheroids were formed as described in Examples 2 and 3, below. FIG. 3 depicts methods to form hybrid spheroids according to embodiments of the present disclosure including a schematic illustration of deriving endothelial cell (iEC) spheroids from hiPSCs and a schematic illustration of generating hybrid spheroids from iNPCs. hMSCs were added to iNPCs for iNPC-MSC-iEC spheroids (method A), before iEC transfer. Or hMSCs were added to the well containing both iNPC spheroids and iEC spheroids for iNPC-iEC-MSC spheroids (method B). hMSCs were labeled with CellTracker Red.

Example 2: Hybrid iNPC-MSC-iEC Spheroid Formation

Human MSCs were pre-labeled with CellTracker Red (2.5 μM, Life Technologies) for 30 min unless otherwise noted. Different numbers of hMSCs were added to day 7 iNPC spheroids (with different seeding densities) for a total of $2\times10^4$ cells (FIG. 3) or directly mixed at day 0 [30]. The ratios of hiPSC:hMSCs were 4:0, 3:1, 2:2, and 1:3 based on initial seeded cell numbers. Then, the day 14 iEC spheroids were transferred into the wells containing day 14 iNPC-MSC spheroids. Different cell ratios for generating hybrid spheroids were iNPC:iEC:MSC=4:2:0, 3:2:1 2:2:2, and 1:2:3 (total $4\times10^4$ per well, n=3-12), referred as Bi-(4:2), Tri-(3:2:1), Tri-(2:2:2), and Tri-(1:2:3) respectively. For some experiments, iNPC only [32, 37], iEC only [16, 46] or MSC only spheroids [28, 47, 48] were used as controls. The hybrid iNPC-MSC-iEC spheroids were maintained in neural differentiation medium for additional 7 days for aggregate fusion.

The iNPC-MSC spheroids and iEC spheroids fused into the aggregates with squared aspect ratio of 0.5-0.7 after 7 days.

Example 3: Hybrid iNPC-iEC-MSC Spheroid Formation

In this example, day 14 iEC spheroids were transferred into the wells containing day 14 iNPC spheroids first (FIG. 3). Immediately after the transfer, hMSCs were added into the wells at different cell densities to maintain ratios of iNPC:iEC:MSC=4:2:0, 3:2:1, 2:2:2, and 1:2:3 (n=3-12). For long-term cultures, day 14 iEC spheroids were transferred into the wells containing day 14 iNPC spheroids to allow aggregate fusion. Then, at 7 days before harvesting, hMSCs were added into the wells at different cell densities to maintain ratios of iNPC:iEC:MSC=4:2:0, 3:2:1 2:2:2, 1:2:3, and 0:2:4. The total culture length ranged from 21 days to 52 days.

For iNPC-iEC-MSC spheroids, hMSCs were added into the well of day 14 iNPC-iEC hybrid spheroids and cultured for another 7 days or MSCs and iEC spheroids were added together to the wells containing iNPC spheroids (FIGS. 4, 5A-5B, and 6A-6C).

Figure 4:
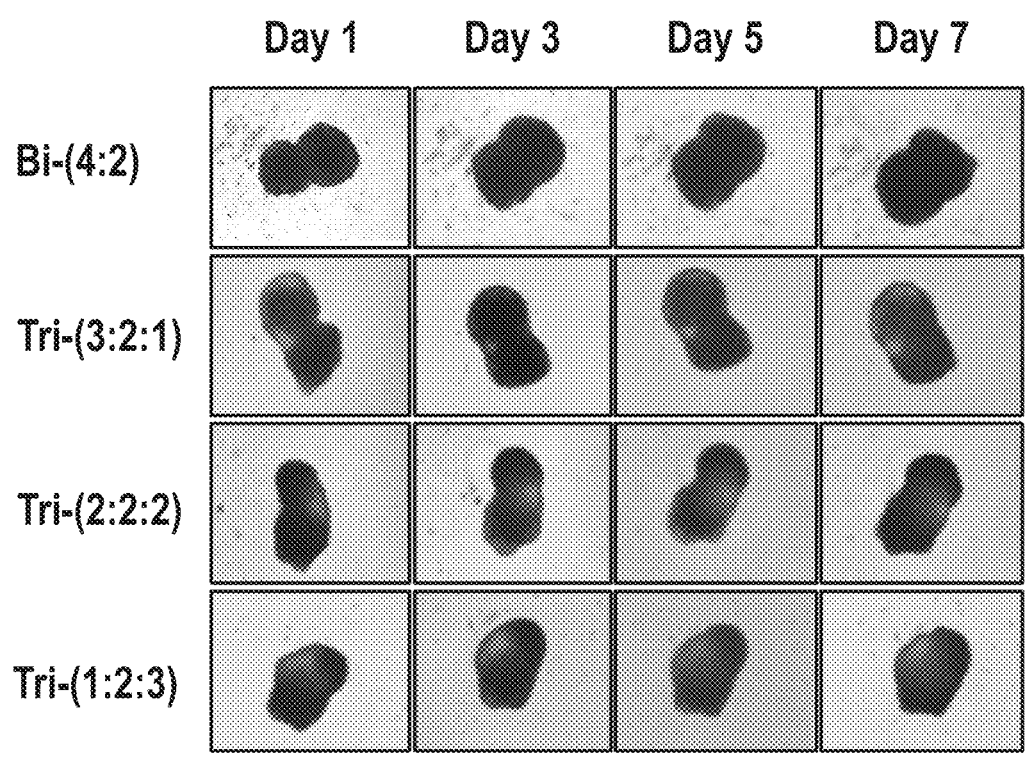
FIG. 4 depicts phase contrast images of iNPC-iEC-MSC spheroids morphology at day 1, 3, 5, and 7 (total day 15-21).

Specifically, FIG. 4 depicts phase contrast images of iNPC-iEC-MSC spheroids morphology at day 1, 3, 5, and 7 (total day 15-21). iEC spheroids and MSCs were added to the preformed iNPC aggregates at the same time. Scale bar: 400 μm.

Figure 5B:
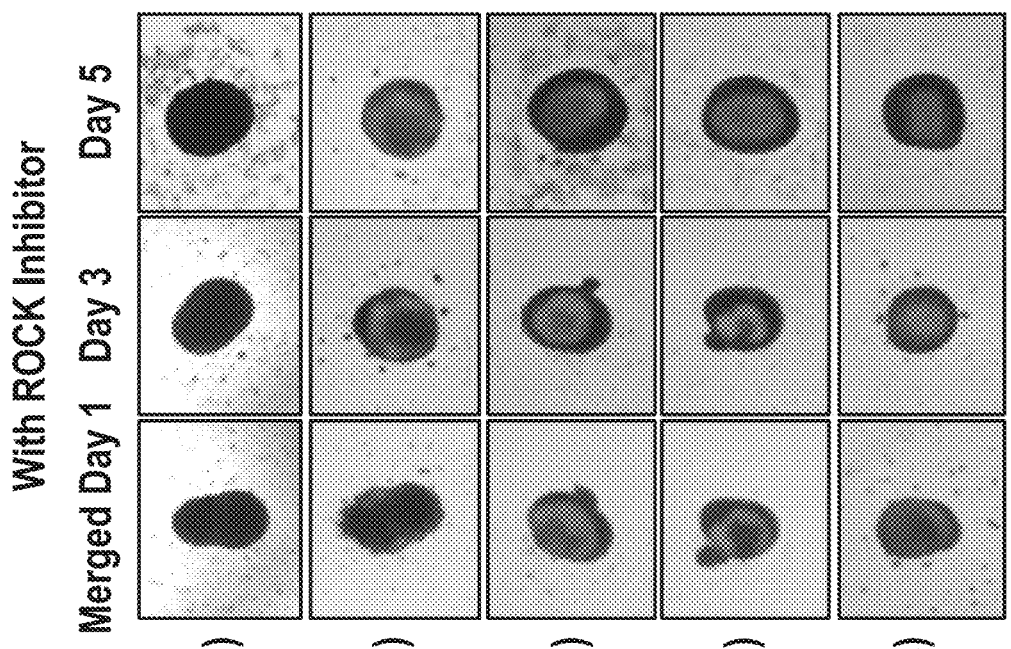
FIGS. 5A-5B depict overlay of phase contrast images (iNPCs and iECs) with fluorescent images (hMSCs) of hybrid spheroids.
Figure 5A:
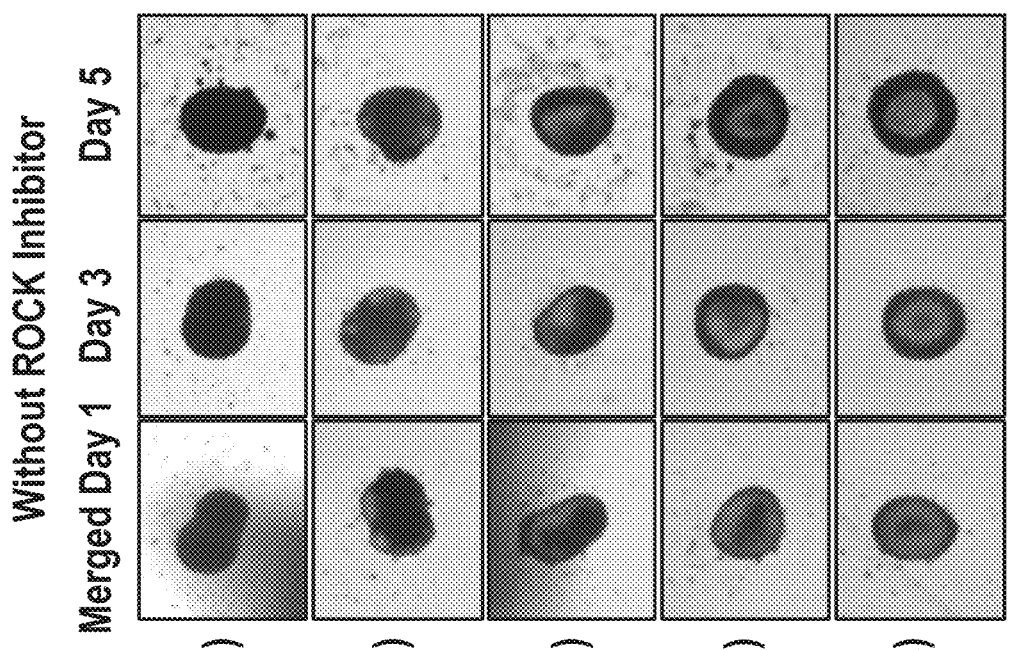

FIGS. 5A-5B depict overlay of phase contrast images (iNPCs and iECs) with fluorescent images (hMSCs) of hybrid spheroids with (FIG. 5A) or without (FIG. 5B) ROCKi Y27632 (10 μM) when MSCs were added to the culture one week after fusion of iNPC spheroids and iEC spheroids. Scale bar: 400 μm.

Figure 6A:
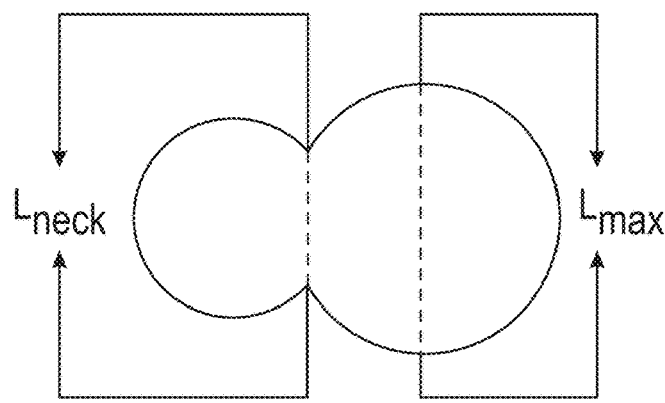
FIGS. 6A-6C depict a schematic illustration of calculation of squared aspect ratio of contact length between two aggregates over maximum diameter and aggregation kinetics.
Figure 6B:
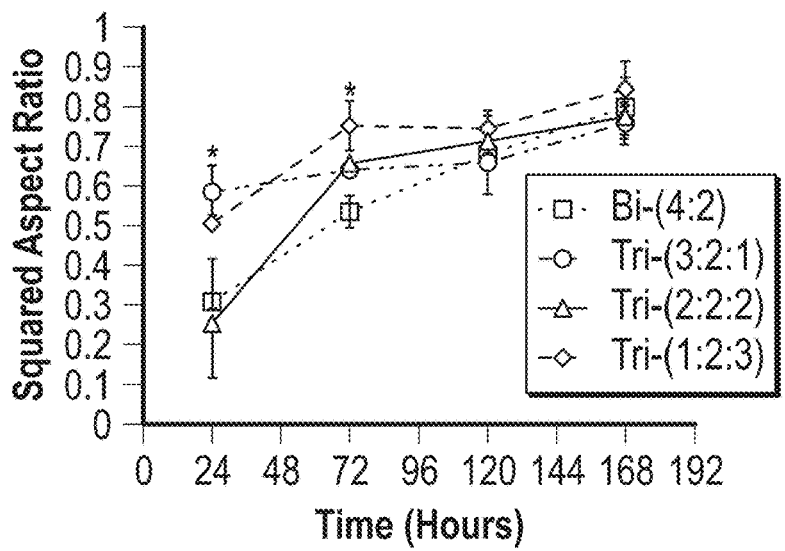

FIG. 6A is a schematic illustration of calculation of squared aspect ratio of contact length between two aggregates over maximum diameter $$\left(\frac{Lneck}{Lmax}\right)^2.$$

Figure 6C:
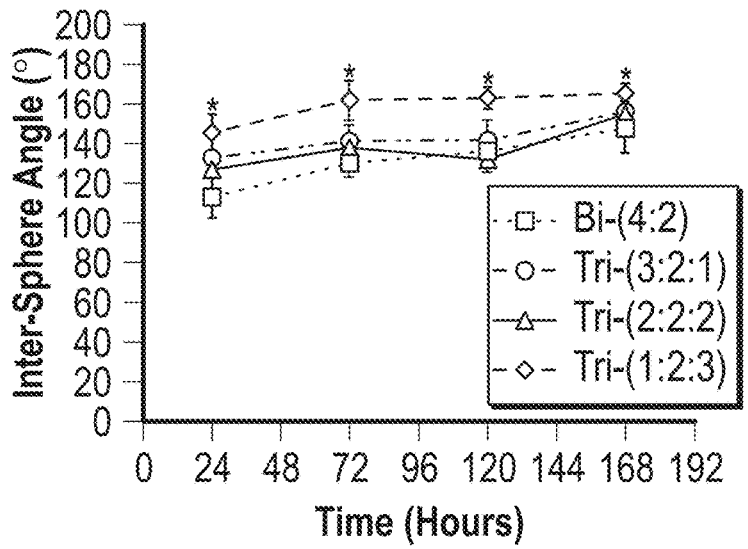
Figure 7A:
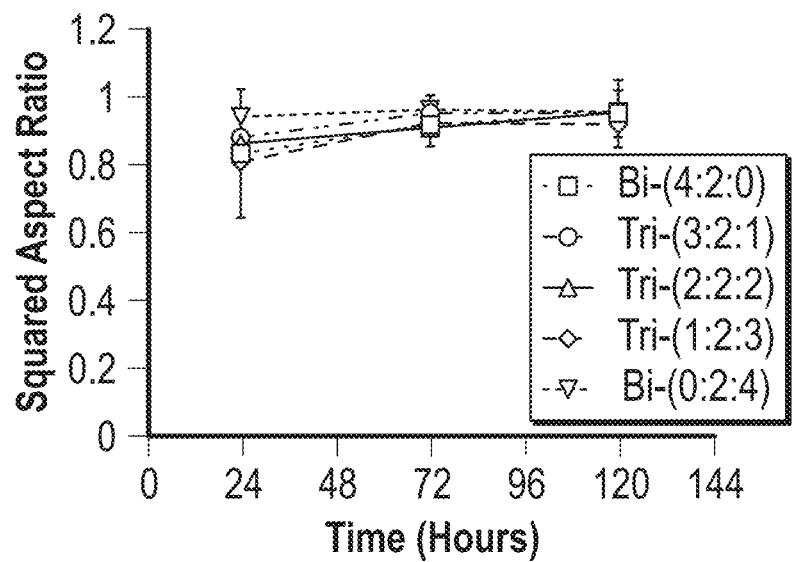
FIGS. 7A-7B depict the aggregation kinetics analyzed in (Ei) and (Eii), respectively.
Figure 7B:
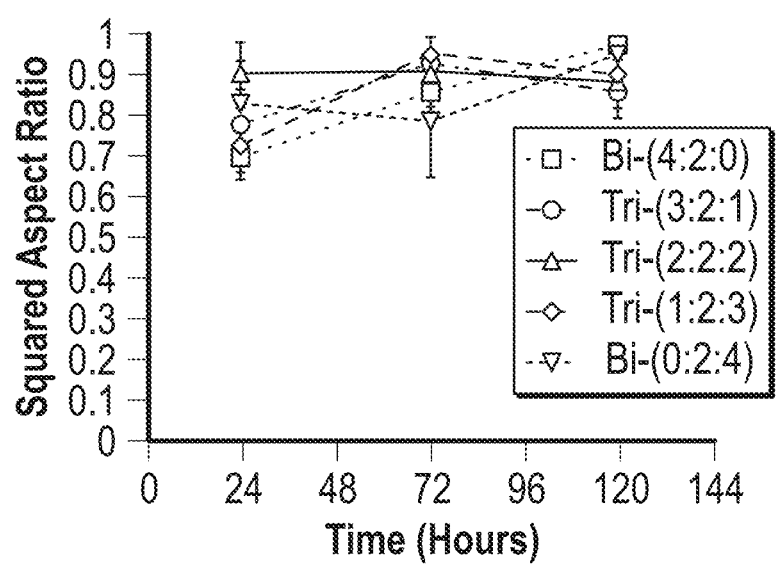

The aggregation kinetics were evaluated by the squared aspect ratio over 7 days (FIG. 6B) and the inter-sphere angle formed by the two aggregates (FIG. 6C).

hMSCs were integrated with the iNPC-iEC hybrid spheroids and migrated toward the spheroid center. The squared aspect ratio was in the range of 0.9-1.0 (FIGS. 7A-7B). Specifically, FIGS. 7A-7B depict the aggregation kinetics were analyzed in (Ei) and (Eii), respectively. *indicates $p<0.05$ for the different test conditions.

The low concentration of ROCKi did not impact the integration of MSCs into iNPC-iEC spheroids. Due to the higher squared aspect ratio (indicating good fusion kinetics), iNPC-iEC-MSC spheroids were mainly used in the following experiments.

The effects of Geltrex (similar to Matrigel, commonly used in organoid formation [3, 54]) or hyaluronic acid (HA) (an ECM component in brain [55]) on the fusion of neural spheroids and vascular spheroids was investigated (FIGS. 8A-8B and 9A-9B).

Specifically, overlay of phase contrast images (iNPC spheroids and iEC spheroids) with fluorescent images (hMSCs) of iNPC-iEC-MSC spheroids with Geltrex at 5% or 10% and aggregation kinetics of hybrid spheroids embedded in Geltrex (5% or 10%) was depicted (not shown).

Overlay of phase contrast images with fluorescent images of iNPC-iEC-MSC spheroids with hyaluronic acid (HA, 0.025 wt % or 0.05 wt %) and aggregation kinetics of hybrid iNPC-iEC-MSC spheroids embedded in 0.025 or 0.05 wt % HA was depicted (not shown).

Figure 8A:
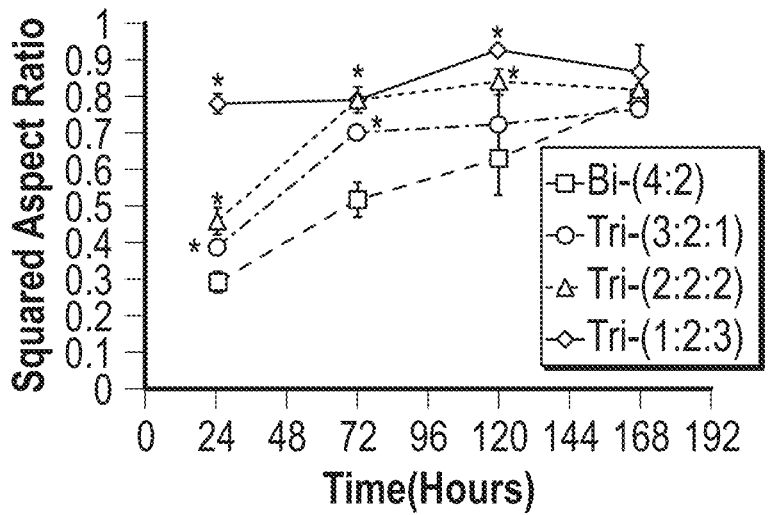
FIGS. 8A-8B depict overlay of phase contrast images (iNPC spheroids and iEC spheroids) with fluorescent images (hMSCs) of iNPC-iEC-MSC spheroids with Geltrex at 5% or 10% and aggregation kinetics.
Figure 8B:
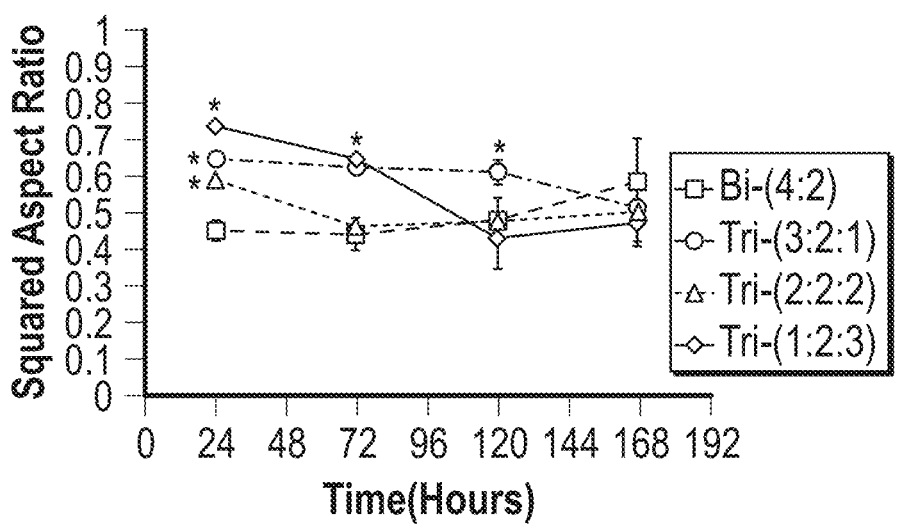
Figure 9A:
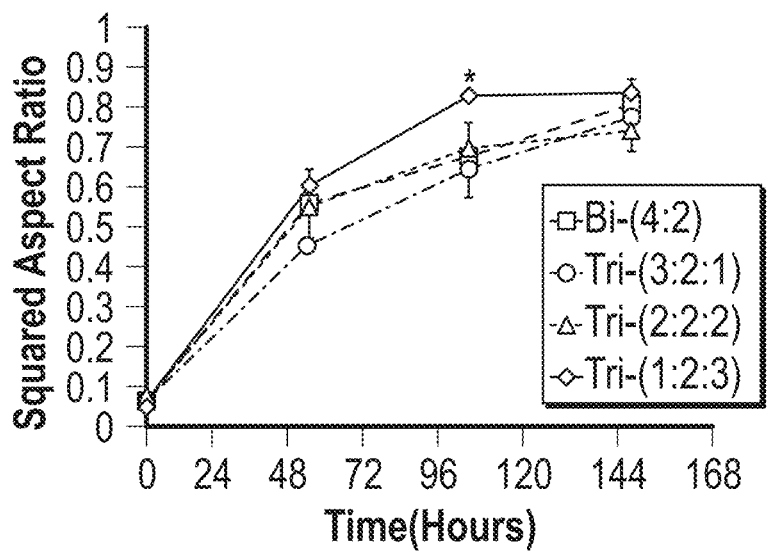
FIGS. 9A-9B depict overlay of phase contrast images with fluorescent images of iNPC-iEC-MSC spheroids with hyaluronic acid (HA, 0.025 wt % or 0.05 wt %) and aggregation kinetics.
Figure 9B:
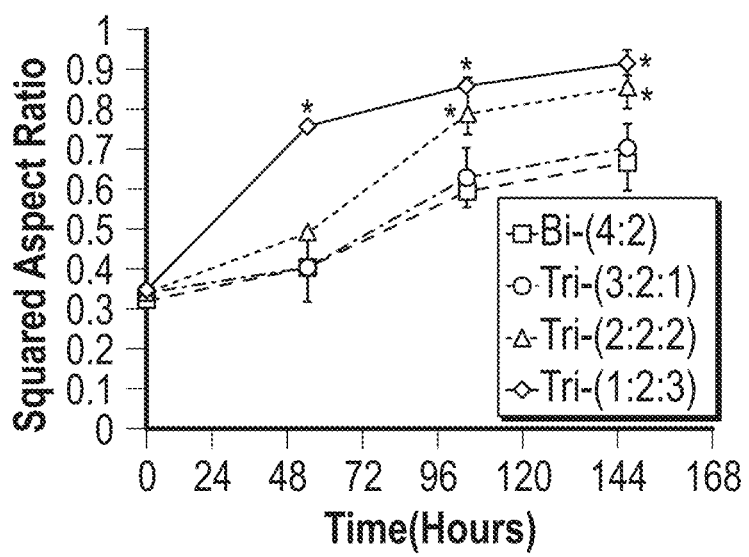

Quantification of squared aspect ratios over 7 days showed a good fusion tendency for 5% Geltrex (0.7-0.9 by day 7), but not for 10% Geltrex (0.4-0.6 by day 7) (FIGS. 8A-8B). For HA treatment, 0.025 wt % HA resulted in squared aspect ratio in the range of 0.7~0.9. But 0.05 wt % HA treatment resulted in lower squared aspect ratios (~0.6 by day 7) for Tri-(2:2:2) and Tri-(1:2:3) groups (FIGS. 9A-9B).

Figure 10A:
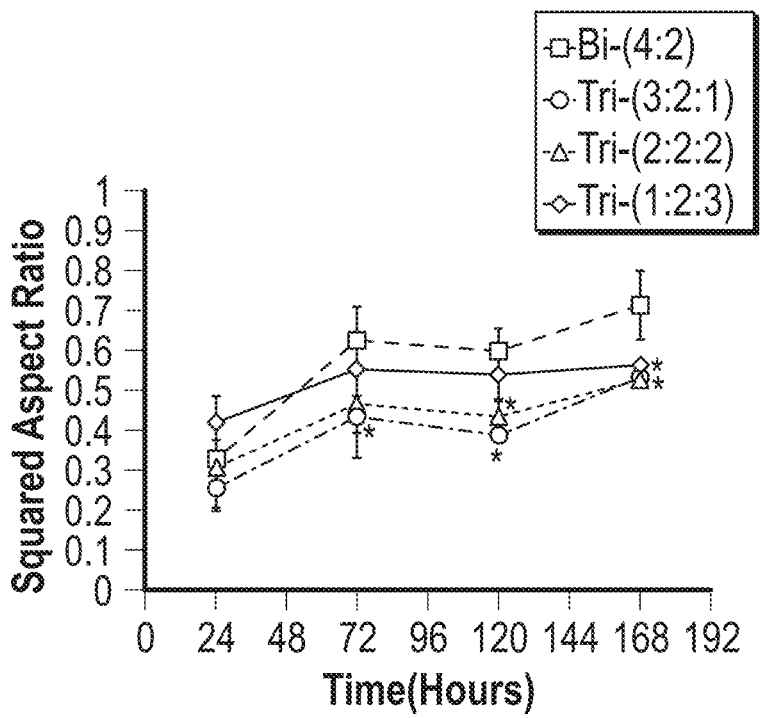
FIGS. 10A-10B depict overlay of phase contrast images and fluorescent images of iNPC-iEC-MSC spheroids with the treatment of ROCKi Y27632 (20 µM or 40 µM); and aggregation kinetics of hybrid spheroids.
Figure 10B:
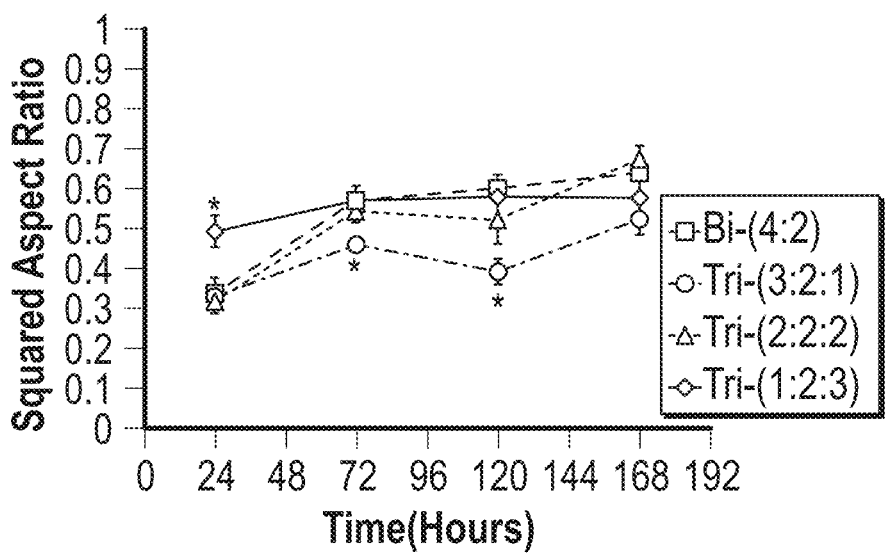

The tendency of two spheroids to fuse was disrupted by ROCKi Y27632 at high concentration (FIGS. 10A-10B). Specifically, overlay of phase contrast images and fluorescent images of iNPC-iEC-MSC spheroids with the treatment of ROCKi Y27632 (20 μM or 40 μM) was depicted (not shown); and aggregation kinetics of hybrid spheroids were treated with Y27632 (20 μM or 40 μM) (FIG. 10A). The time when three cell types were co-cultured (day 14) was counted as day 0. Day 1-7 equals total day 15-21. Scale bar: 400 μm. *indicates $p<0.05$ for the different test conditions.

The aspect ratios (0.5-0.7) of 20 μM or 40 μM ROCKi treatments showed a plateau over 7 days (FIGS. 10A-10B). Without intending to be bound by any particular theory, it is believed that these results indicate that 5% Geltrex and 0.025 wt % HA promote spheroid fusion.

Example 4: Effects of Geltrex, Hyaluronic Acid (HA) Hydrogels, and ROCKi Y27632 on Spheroid Fusion To form hHA hydrogels, 1% (w/v) HA from Sigma Aldrich solution was reacted with a 5-fold molar excess amount of methacrylic anhydride (MA) from Sigma Aldrich for 15 h in the dark at 4° C. The final product was collected by precipitating the solution in 5-fold volume of ethanol twice, and was then purified by dialysis using a membrane (3.5 kDa Mw cut-off, Thermofisher) to remove unreacted reagents. The purified MA-HA was filtered, lyophilized, and stored at −20° C. until further use [49]. Next, $^1$H-NMR spectroscopy (a Bruker 500M spectrometer at 200 MHz) was used to analyze and the degree of methacrylation. For culture experiments, day 14 iEC spheroids were transferred to the wells containing day 14 iNPC spheroids, at the same time hMSCs were added into the wells at different ratios (iNPC:iEC:MSC=4:2:0, 3:2:1 2:2:2, and 1:2:3). The aggregates were cultured in medium with different concentrations of Geltrex (5%, or 10% v/v) or HA hydrogel (0.025 or 0.05 wt %) or treated with ROCK inhibitor Y-27632 (20 or 40 μM) at day 0. The morphology of hybrid spheroids were captured over 7 days by a phase contrast microscope.

Images of spheroid fusion were captured over time by a phase contrast microscope. The captured images were converted to binary images using ImageJ software (rsb.info.nih.gov/ij) and analyzed with the "particle analysis tool". Through particle analysis, the squared aspect ratio of contact length between the two aggregates over maximum diameter (FIG. 6A) was determined to indicate the aggregate fusion process. The inter-sphere angle was measured as the intersecting angle between the tangent lines of two contacted spheroids to the touch point. For some experiments, the number of branching points and the total tube length in the area were evaluated.

Example 5: Analysis of Hybrid Spheroids

Biochemical Assays

First, an MTT assay was conducted. The spheroids of Examples 2 and 3 were incubated with 5 mg/mL 3-(4,5-Dimethylthiazol-2-yl)-2,5-diphenyltetrazolium bromide (MTT, Sigma) solution at day 7 after three cell types were co-cultured unless otherwise noted. The absorbance of the samples was measured at 500 nm using a microplate reader (Biorad, Richmond, Calif.).

Next, a DNA assay was conducted. The DNA content of the hybrid spheroids of Examples 2 and 3 was determined at day 7 after three cell types were co-cultured unless otherwise noted. A DNA standard was prepared by dissolving salmon testes DNA in TEX (10 mM Tris, 1 mM EDTA, 0.1% Triton X-100 at pH 8) and a standard curve was constructed for each assay. The aggregates were lysed with 0.1 mg/mL proteinase K (Fisher Scientific, Pittsburgh, Pa.) at 50° C. overnight. The lysates (100 μL) were mixed with 100 μL of Picogreen (Molecular Probes) in a 96-well plate. The plate was incubated for 5 min in the dark and then read on a fluorescent plate reader (FLX800, Bioinstrument Inc., Winooski, Vt.).

Next, an enzyme-linked immunosorbent assay (ELISA) assay was conducted. To quantify the growth factors secreted by different spheroids, culture supernatants were collected at day 7 after three cell types were co-cultured. Concentrations of FGF-2, PGE2, VEGF, and transforming growth factor (TGF)-β1 were measured by ELISA according to the manufacturers' instructions (R&D Systems, Minneapolis, Minn. for PGE2 and FGF-2; Life Technologies for TGF-β1 and VEGF). Briefly, the samples were added into 96-wps and incubated with primary/secondary antibody solution conjugated with horseradish peroxidase for 2-3 hours. After washing, 3,3',5,5'-tetramethylbenzidine substrate solution was added, and the mixture was incubated for 30 min. The absorbance units were measured using a microplate reader (Bio-Rad, Richmond, Calif.).

Immunocytochemistry of Hybrid Spheroids

The hybrid spheroids of Examples 2 and 3 were fixed with 4% paraformaldehyde (PFA) and permeabilized with 0.2-0.5% Triton X-100. The samples were then blocked for 30 min and incubated with various mouse or rabbit primary antibodies, listed in Table 1 below for four hours.

TABLE 1

| Antibodies | | | | |
|---|---|---|---|---|
| Cells | Primary Antibody | Origin/ Isotype | Supplier/Cat# | Dilution |
| Neural cells | Nestin | Rabbit IgG | Sigma, N5413 | 1:100 |
| | FOXG1 | Rabbit IgG | ThermoFisher, PA5-26794 | 1:100 |
| | TBR1 (layer VI) | Rabbit IgG | ABCAM, ab31940 | 1:200 |
| | SATB2 (layer IV) | Mouse IgG$_1$ | ABCAM, ab51502 | 1:5 |
| | BRN2 (layer III) | Goat IgG | Santa Cruz, sc-6029 | 1:200 |
| | β-tubulin III | Mouse IgG$_1$ | Millipore, MAB1637 | 1:200 |
| | MAP-2 | Rabbit IgG | ABCAM, ab32454 | 1:200 |

TABLE 1-continued

| Antibodies | | | | |
|---|---|---|---|---|
| Cells | Primary Antibody | Origin/ Isotype | Supplier/Cat# | Dilution |
| | ISL1 | Rabbit IgG | Millipore, AB4326 | 1:300 |
| | HOXB4 | Rabbit IgG | ABCAM, ab76093 | 1:200 |
| Synaptic markers | Glutamate | Rabbit IgG | Sigma, G6642 | 1:1000 |
| | GABA | Rabbit IgG | Sigma, A2052 | 1:1000 |
| | Synapsin I | Rabbit IgG | Millipore, 574777 | 1:500 |
| | PSD95 | Rabbit IgG | Life Technologies, 51-6900 | 1:200 |
| Astrocytes | GFAP | Mouse IgG$_1$ | Millipore, MAB360 | 1:400 |
| Endothelial cells | KDR | Mouse IgG$_1$ | Millipore, 05-554 | 1:100 |
| | CD31 | Goat polyclonal IgG | Santa Cruz, sc-1506 | 1:200 |
| | VE-cadherin | Goat polyclonal IgG | Santa Cruz, sc-6458 | 1:200 |
| | ZO-1 | Mouse IgG$_1$ | Life Technologies, 33-9100 | 1:100 |
| Cell-cell adhesion | E-cadherin | Mouse-IgG$_1$ | Millipore; MABT26 | 1:100 |
| | Collagen IV | Rabbit IgG | ABCAM, ab6586 | 1:200 |
| | Laminin | Rabbit IgG | ABCAM, ab11575 | 1:200 |
| | CSPG | Mouse IgM | Life Technologies, MA1-83055 | 1:100 |
| | Hyaluronic acid | Sheep IgG | Life Technologies, PA1-85561 | 1:50 |
| Proliferation | BrdU | Mouse IgG$_1$ | Life Technologies, 03-3900 | 1:200 |
| Secondary | Alexa 488, goat anti-mouse IgG1 | — | Life Technologies, A-21121 | 1:200 |
| | Alexa 488, goat anti-rabbit IgG | — | Life Technologies, A-11034 | 1:200 |
| | Alexa 488, goat anti-mouse IgM | — | Life Technologies, A-21042 | 1:200 |
| | Alexa 594, donkey anti-sheep IgG | — | Life Technologies, A-11016 | 1:400 |
| | Alexa 594, goat anti-rabbit IgG | — | Life Technologies, A-11012 | 1:400 |
| | Alexa 594, donkey anti-goat IgG | — | Life Technologies, A-11058 | 1:400 |

For surface markers, no permeabilization was performed. After washing, the cells were incubated with the corresponding secondary antibody: Alexa Fluor® 488 goat anti-Mouse IgG$_1$, Alexa Fluor® 488 or 594 goat anti-Rabbit IgG, or 594 donkey anti-goat IgG (Life Technologies) for one hour. The samples were counterstained with Hoechst 33342 and visualized using a fluorescent microscope (Olympus IX70, Melville, N.Y.) or a confocal microscope (Zeiss LSM 880).

Histology

For histology, various spheroids/organoids (day 21 or day 47, described in Examples 2 and 3 above) were fixed in 10% formalin, dehydrated, and embedded in paraffin wax. Next, sections of 10 μm were cut and stained with Lerner-2

Hematoxylin (Lerner Laboratories, Pittsburgh, Pa.) and Eosin-Y w/Phloxine (Richard-Allan Scientific, Kalamazoo, Mich.) [47]. The sections were also stained with anti-CD31, β-tubulin III, zona occludens 1 (ZO-1), HOXB4, TBR1, SATB2, BRN2, Collagen IV and laminin to show cellular distribution and cortical layer formation. Images were captured with an Olympus IX70 microscope with MagnaFire SP 2.1B software or a confocal microscope (Zeiss LSM 880).

Hybrid spheroids were re-plated to investigate their cellular composition (FIGS. 21A-21D).

The control images for histology images in FIGS. 21A-21D were produced with BRN2/Hoechst and MAP2/Hoechst for iNPC spheroids and CD31/Hoechst, VE-cadherin/Hoechst, and ZO1/Hoechst for iEC spheroids (not shown). Enlarged images for neural marker β-tubulin III/ vascular marker CD31 expression in hybrid spheroids of FIG. 22A was produced (not shown).

The expression of vascular markers, CD31 and VE-cadherin, was observed for all the groups. The fused spheroids also expressed ZO-1, the tight junction protein of brain microvascular cells (not shown). Co-staining of CD31 and Nestin showed that CD31$^+$ cells interacted with the Nestin$^+$ neural cells (not shown). The expression of deep cortical layer VI marker TBR1 (and a little BRN2 expression) indicated the cortical identity of the hybrid spheroids, although hindbrain marker HOXB4 was also expressed at this stage.

Specifically, the neural and vascular marker expression of hybrid spheroids was depicted (not shown). Day 21 hybrid spheroids were replated for three days and immunocytochemistry was performed. Fluorescent images of vascular markers, including CD31/Hoechst for endothelial cells, VE-cadherin/Hoechst for later stage of endothelial cells, and ZO1/Hoechst, the tight junction protein expressed by brain microvascular endothelial cells were produced (not shown). Fluorescent images of neural markers, including Nestin for neural progenitors, HOXB4 (a hindbrain marker), TBR1 (forebrain deep cortical layer VI) and BRN2 (forebrain cortical superficial layer II-IV) were produced (not shown). Fluorescent images of MAP2 (more mature neurons), GFAP (astrocyte progenitors) and E-cadherin (cell-cell interactions) were produced (not shown). Extensive MAP2 signals showed the mature neuron population, while the expression of GFAP indicated the existence of glial progenitors. Cells from tri-cultured spheroids had more E-cadherin expression (heterogeneous signal intensity), while Bi-(4:2) group had homogenous expression.

Histological sections were evaluated to assess the in situ distribution and localization of iECs and neural cells within the hybrid spheroids (not shown). Numerous CD31$^+$ vascular cells interacted with β-tubulin III' neurons were observed throughout the spheroids (not shown). In addition, the distribution of CD31 was more homogenous for Tri-(2:2:2) and Tri-(1:2:3) groups. More ZO-1 expression was observed for tri-cultured spheroids. Confocal images of intact spheroids of FOXG1 and CD31 showed the FOXG1$^+$ layers and the lumens of CD31$^+$ cells (not shown). The expression of TBR1 inside the fused spheroids was observed, but the expression of BRN2 was minimal at this early stage (not shown).

Figure 15:
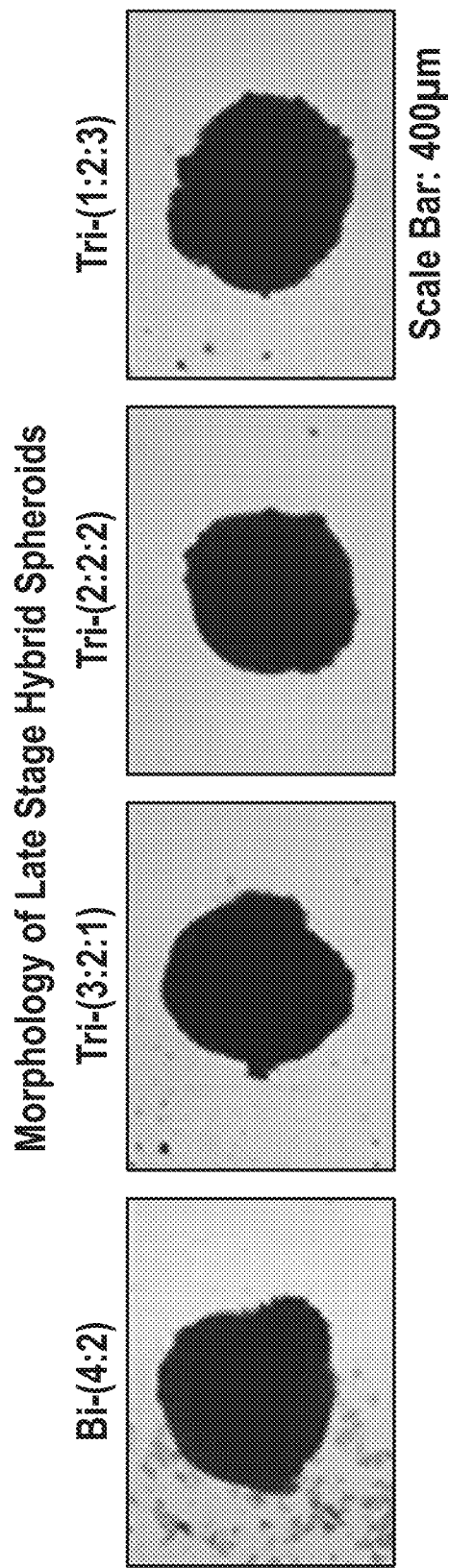
FIG. 15 depicts morphology and histology characterizations for early (day 21) and late (day 47) stage hybrid spheroids.

Specifically, FIG. 15 depicts morphology and histology characterizations for early (day 21) and late (day 47) stage hybrid spheroids. Images of histology thin sections of day 21 spheroids were produced using cortical layer marker TBR1/BRN2, HOXB4 and Hoechst (not shown). Phase contrast images of hybrid spheroid morphology at day 40 (FIG. 15). Scale bar: 400 Collagen IV, laminin, chondroitin sulfate proteoglycans (CSPG), and hyaluronic acid (HA) expression for hybrid spheroid histological sections at day 47 was observed (not shown).

Figure 21A:
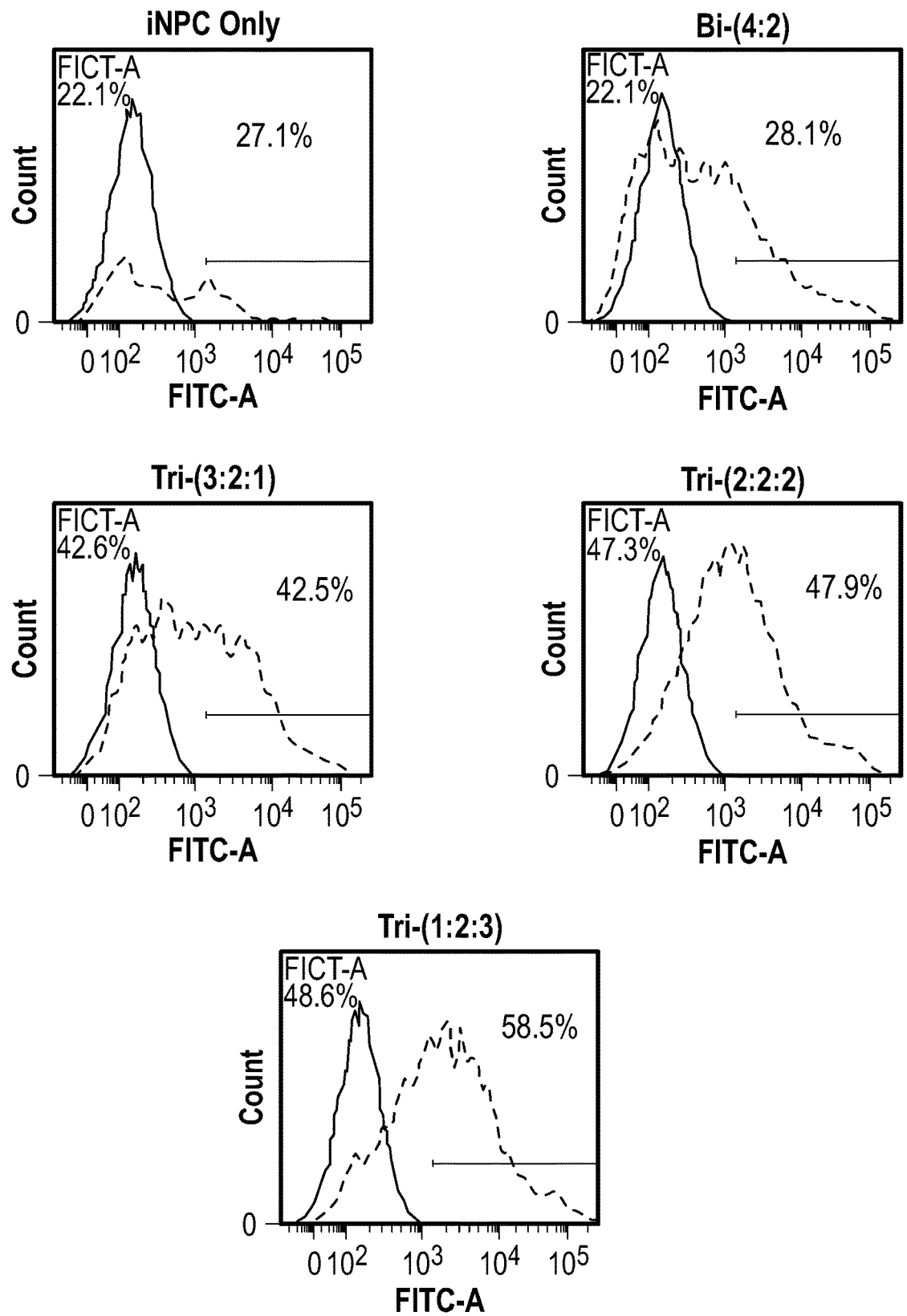
FIGS. 21A-21D depict histology images of early and late stage hybrid spheroids and quantification by flow cytometry.

In addition, one side of spheroids expressed HOXB4. The quantification of β-tubulin III showed the higher level for tri-cultured spheroids (i.e., 47.2±6.7%, 50.2±3.2%, 63.4±6.8% for Tri-(3:2:1), Tri-(2:2:2), Tri-(1:2:3) respectively) than Bi-(4:2) group (18.9±12.8%) (FIGS. 21A, 21C).

Figure 21B:
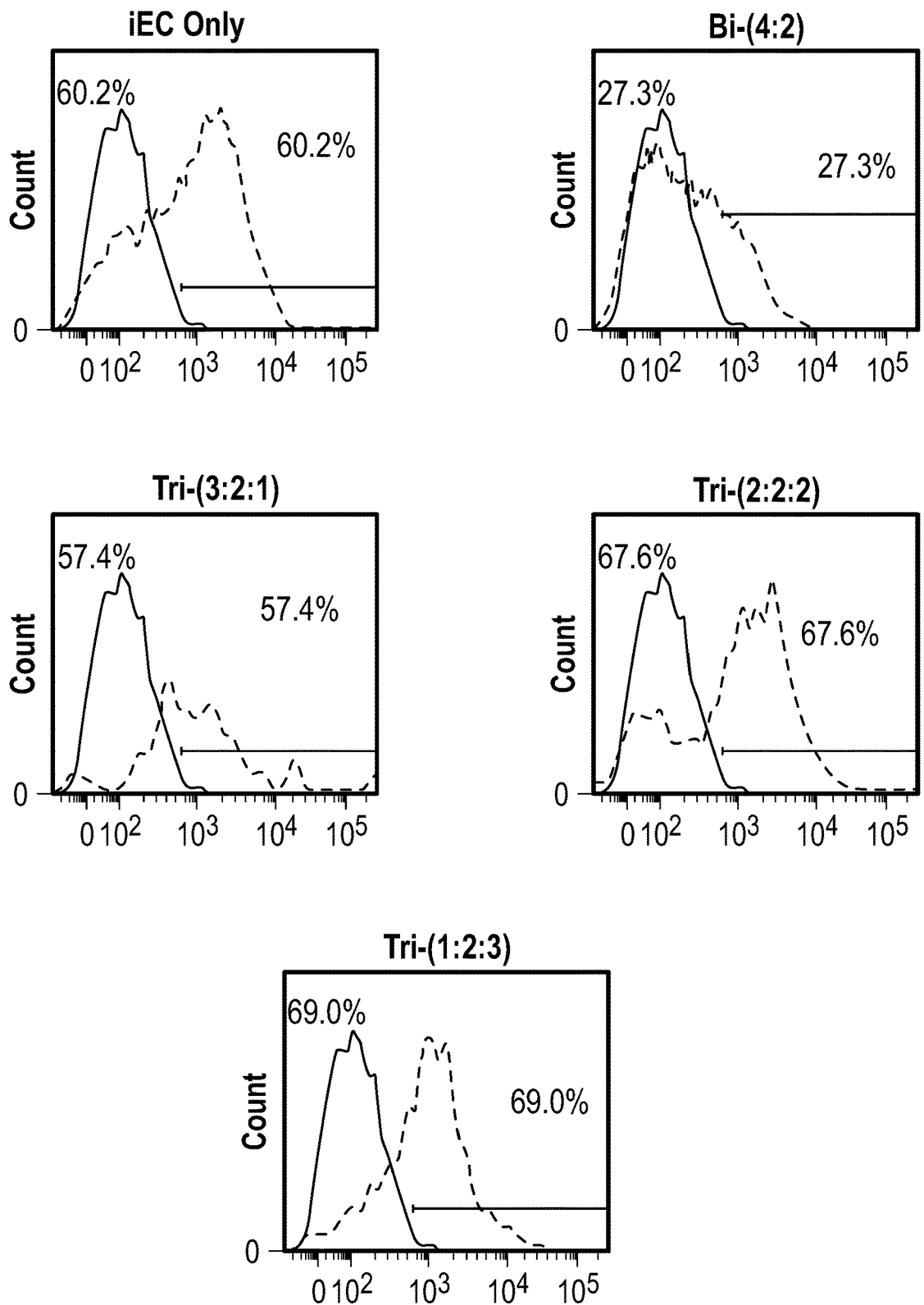
Figure 21C:
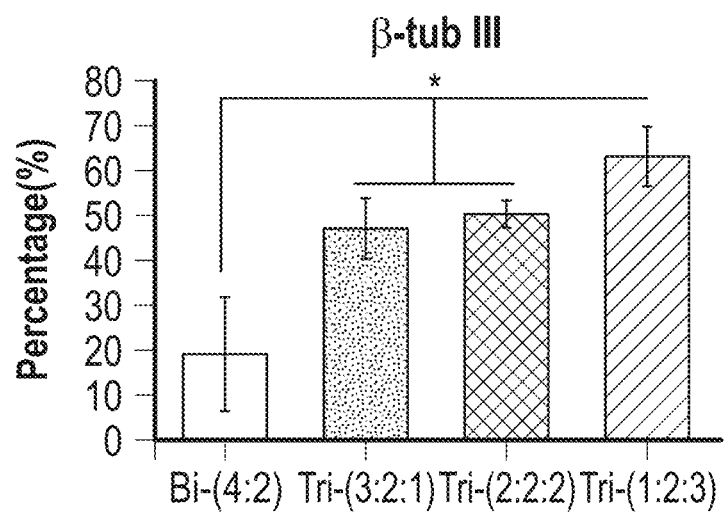

Specifically, FIGS. 21A-21D depict histology images of early and late stage hybrid spheroids and quantification by flow cytometry. Images of histology thin sections of spheroids (total day 21) showed the expression of β-tubulin III and vascular marker CD31, ZO1 (not shown). Confocal images of histology thin sections of spheroids (total day 47) for β-tubulin III and vascular marker CD31 were taken (not shown). Confocal images of day 21 spheroids for FOXG1 and CD31 were taken (not shown). Flow cytometry histograms for day 21 iEC spheroids, iNPC spheroids, or tri-cultured spheroids are depicted for β-tubulin III (FIG. 21A) and CD31 (FIG. 21B). Flow cytometry quantification of β-tubulin III (β-tub III, n=3) (FIG. 21C). Flow cytometry quantification of CD31 (n=3) (FIG. 21D). *indicates p<0.05 for the different test conditions. Images of histology thin sections of late stage spheroids (total day 47) showed the expression of cortical layer markers: TBR1/SATB2, BRN2/SATB2 (not shown).

Figure 21D:
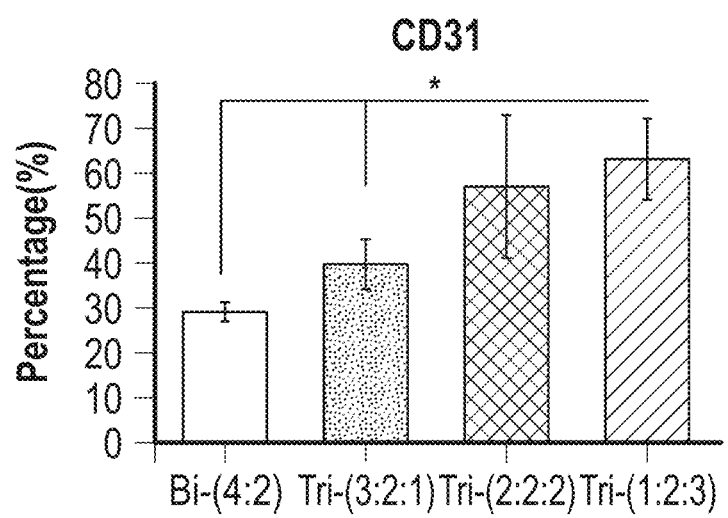

Similarly, higher CD31 expression was observed for the tri-cultured spheroids (i.e., 38.9±5.7%, 55.8±15.8%, 61.1±1.2% for Tri-(3:2:1), Tri-(2:2:2), Tri-(1:2:3) respectively) than Bi-(4:2) group (28.6±1.8%) (FIGS. 21B, 21D). Late stage histology of day 47 forebrain organoids showed the development of superficial cortical layer II-IV indicated by SATB2 and BRN2 expression (FIG. 15). For Bi-(4:2), SATB2 layer was under the TBR1 layer, while the two layers mixed together for Tri-(3:2:1) and Tri-(2:2:2). For Tri-(1:2:3), the TBR1 layer moved toward the center of organoids while the SATB2 layer moved to the surface, according to "inside-out" cortical layer development [32]. Base membrane proteins Collagen IV and laminin as well as brain matrix chondroitin sulfate proteoglycans and hyaluronic acid were detected in day 47 hybrid organoids (not shown). These results indicate that tri-culture promotes neural and vascular differentiation, and the better ratio is Tri-(1:2:3) group.

Flow Cytometry

To quantify the levels of various markers, the cells were harvested by trypsinization and analyzed by flow cytometry [50]. Briefly, 1×10$^6$ cells per sample were fixed with 4% PFA and washed with staining buffer (2% FBS in PBS). The cells were permeabilized with 100% cold methanol, blocked, and then incubated with primary antibodies against β-tubulin III, KDR, CD31, and VE-cadherin, followed by the corresponding secondary antibody Alexa Fluor 488 goat anti-Mouse IgG$_1$ (for β-tubulin III, KDR), or Alexa Fluor 594 donkey anti-goat IgG (for CD31, VE-Cadherin [51]). For surface markers, no permeabilization was performed. The cells were acquired with BD FACSCanto™ II flow cytometer (Becton Dickinson) and analyzed against isotype controls using FlowJo software.

Reverse Transcription Polymerase Chain Reaction (RT-PCR) Analysis

Total RNA was isolated using the RNeasy Mini Kit (Qiagen, Valencia, Calif.) according to the manufacturer's protocol followed by the treatment of DNA-Free RNA Kit (Zymo, Irvine, Calif.) [52]. Reverse transcription was carried out using 2 μg of total RNA, anchored oligo-dT primers (Operon, Huntsville, Ala.), and Superscript III (Invitrogen, Carlsbad, Calif.) (according to the protocol of the manufacturer). Primers specific for target genes were designed using the software Oligo Explorer 1.2 (Genelink, Hawthorne, N.Y.), and are shown in Table 2 below:

TABLE 2

Primer Sequences for Target Genes

| Gene | Forward primer 5' to 3' | Reverse primer 5' to 3' |
|---|---|---|
| TBR1 | CCCCCTCGTCTTTCTC TTACC | TAATGTGGAGGCCGA GACTTG |
| HOXB4 | AATTCCTTCTCCAGCT CCAAGA | CCTGGATGCGCAAAG TTCA |
| Nkx2.1 | GAGTCCAGAGCCATGT CAGC | GCATAAAACAGCTTT GGGGTGT |
| MMP2 | CATCGCTCAGATCCGT GGTG | GCATCAATCTTTTCC GGGAGC |
| MMP3 | CCATCTCTTCCTTCAG GCGT | ATGCCTCTTGGGTAT CCAGC |
| Notch-1 | CACTGCTGCCCTCCCC GTTC | TTCAGGTGCCCGATG CCCAG |
| GLUT-1 | AGCAACTGTGTGGTCC CTACG | AAGGTCCGGCCTTTA GTCTCA |
| BCRP | CAGGTGTGCGTCAGAA TCATC | TCCAGGAGTGGTCAG ATTCCTT |
| PGP | ACCACTCTCCCACCTC CCTTA | TTTAGCTGGGCTGCG TTTACA |
| β-actin | GTACTCCGTGTGGATC GGCG | AAGCATTTGCGGTGG ACGATGG |

The gene β-actin was used as an endogenous control for normalization of expression levels. Real-time RT-PCR reactions were performed on an ABI7500 instrument (Applied Biosystems, Foster City, Calif.), using SYBR1 Green PCR Master Mix (Applied Biosystems). The amplification reactions were performed as follows: 2 min at 50° C., 10 min at 95° C., and 40 cycles of 95° C. for 15 sec and 55° C. for 30 sec, and 68° C. for 30 sec. Fold variation in gene expression was quantified by means of the comparative Ct method: $2^{-(C_t\ treatment - C_t\ control)}$, which is based on the comparison of expression of the target gene (normalized to the endogenous control β-actin) between the hybrid spheroids and the spheroids of NPC only.

Figure 17A:
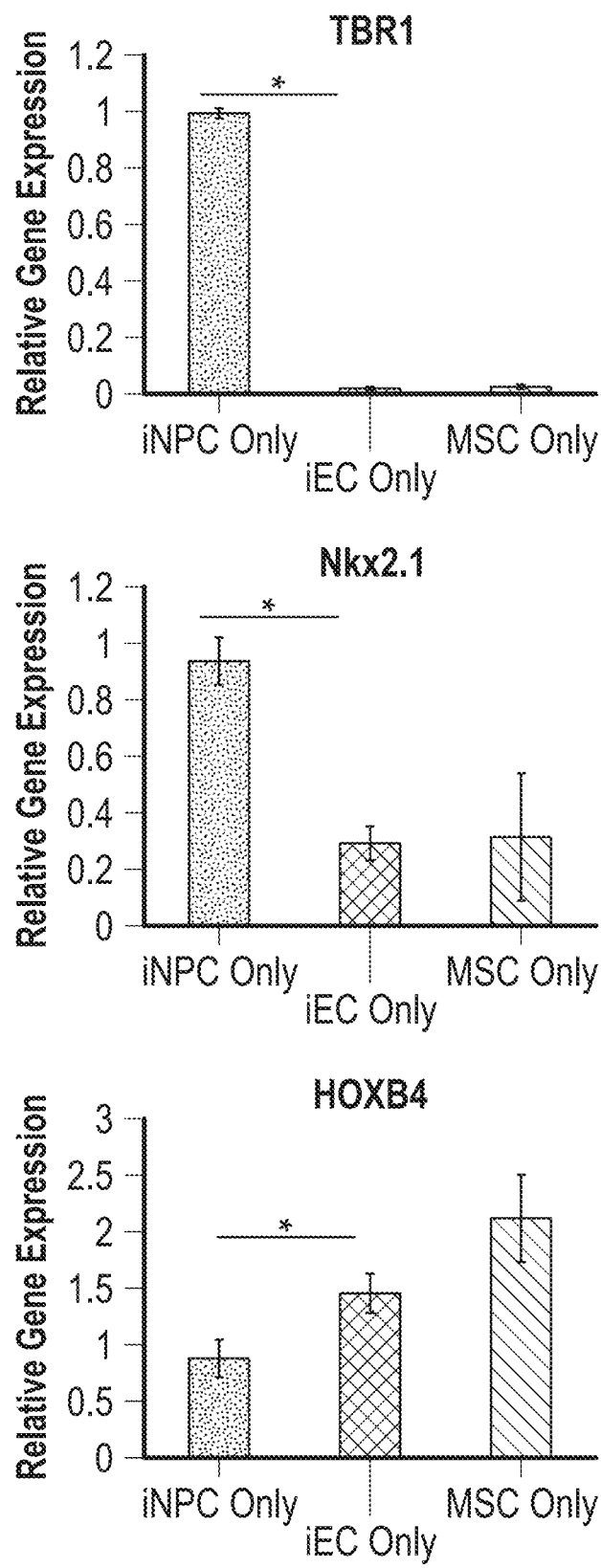
FIGS. 17A-17C depict RT-PCR analysis for iEC and hMSC controls compared to iNPC group.
Figure 17B:
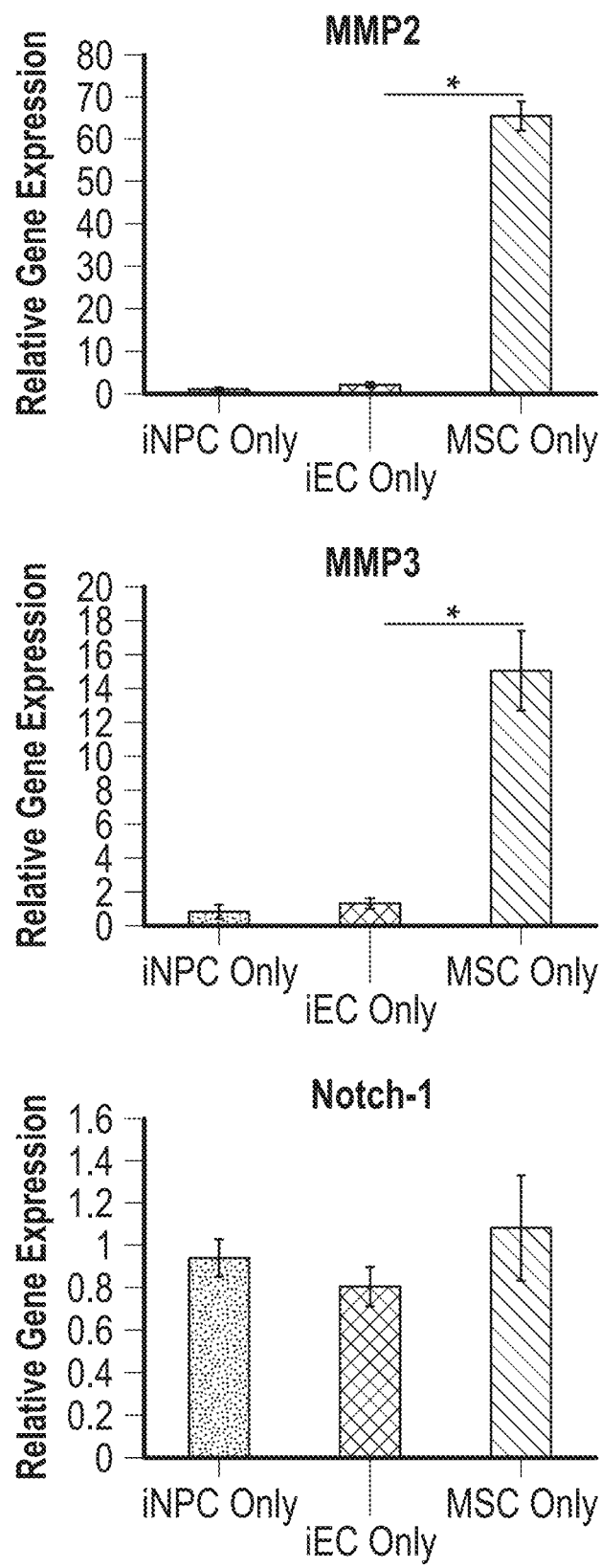
Figure 17C:
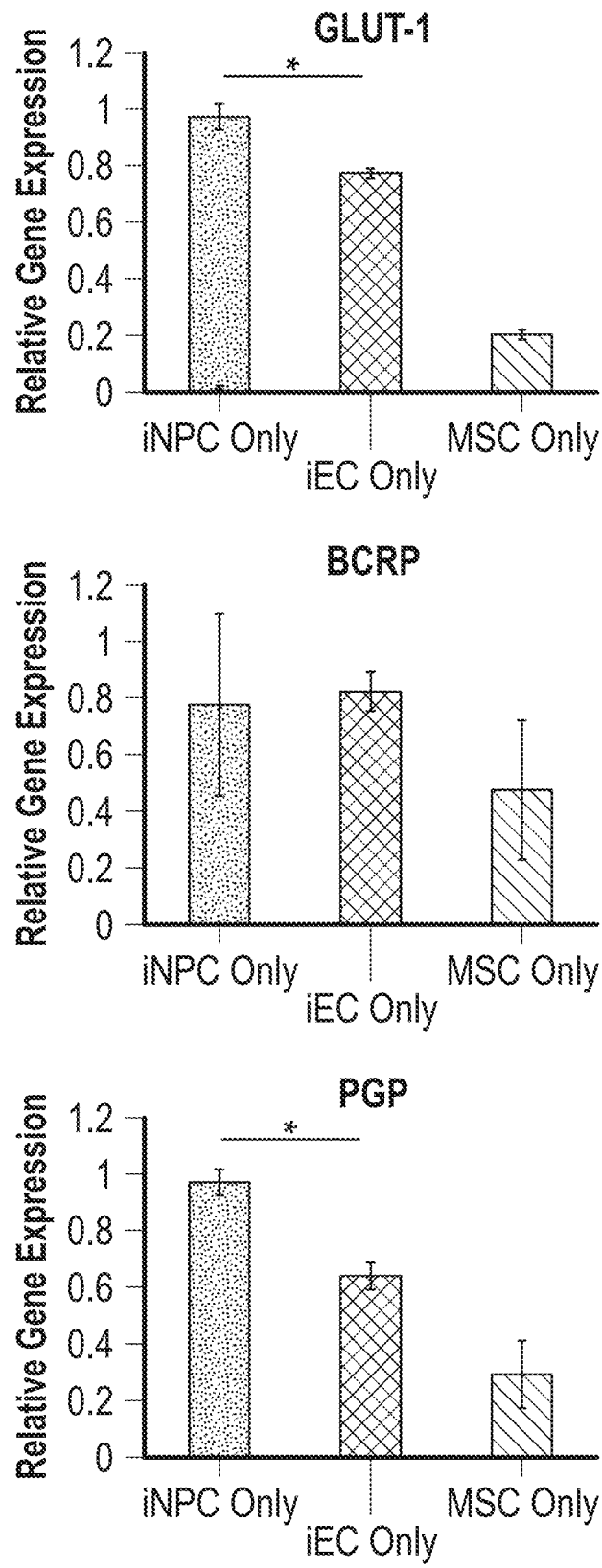

Gene expression of brain regional markers TBR1, HOXB4, and Nkx2.1 were determined for day 21 hybrid spheroids (FIGS. 22A-22I and 17A-17C). Specifically, FIGS. 17A-17C depict RT-PCR analysis for iEC and hMSC controls compared to iNPC group. Brain regional marker genes; TBR1 and Nkx2.1 were the highest for the iNPC group as expected (FIG. 17A). For HOXB4, it may not be a specific hindbrain marker. Matrix remodeling and cell-cell communication genes; MMP2 and MMP3 were the highest for the MSC group as expected, then iEC group, and iNPC group (FIG. 17B). Blood-brain barrier-related genes (FIG. 17C). GLUT-1 and PGP were the highest for the iNPC group, lowest for the MSC group. The iECs differentiation protocol used in this study generate the comment ECs, not the brain microvascular ECs. *indicates p<0.05.

Figure 22A:
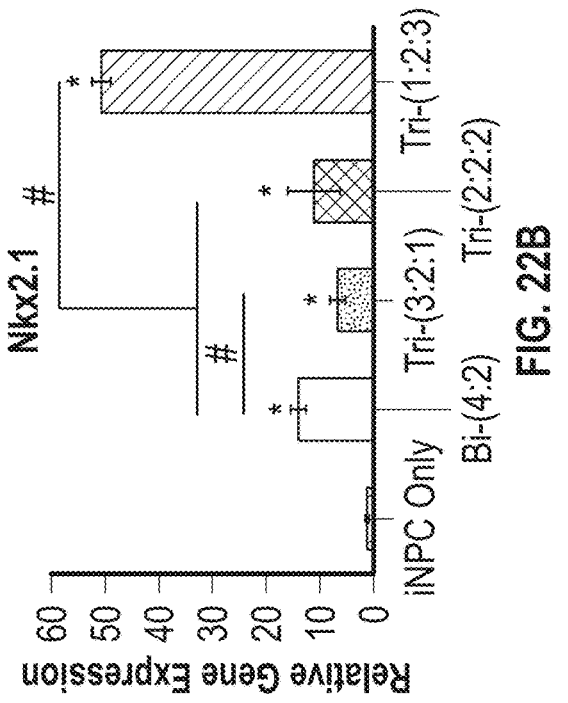
FIGS. 22A-22I depict the results of RT-PCR analysis of gene expression of hybrid spheroids.

The expression level of cortical deep layer VI marker TBR1 increased with the abundance of hMSCs in the hybrid spheroids, i.e., 1.74±0.11, 1.63±0.17, 3.39±0.22, 4.88±0.38 fold for Bi-(4:2), Tri-(3:2:1), Tri-(2:2:2), Tri-(1:2:3) respectively (FIG. 22A).

Figure 22B:
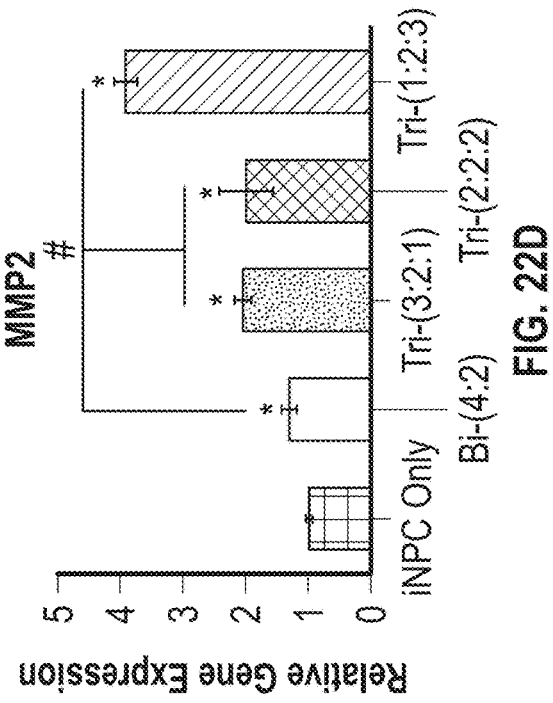
Figure 22C:
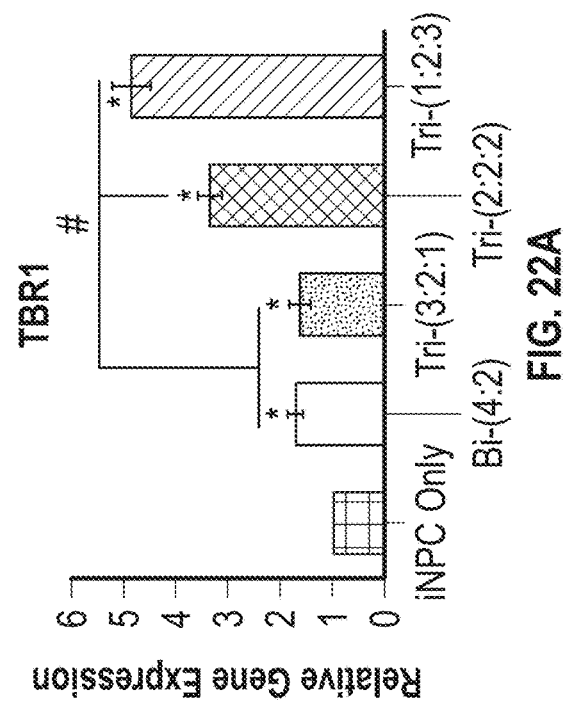
Figure 22D:
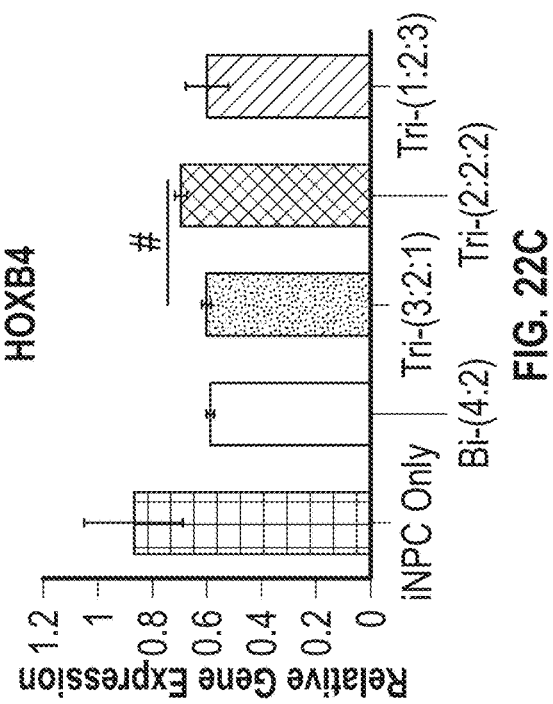
Figure 22E:
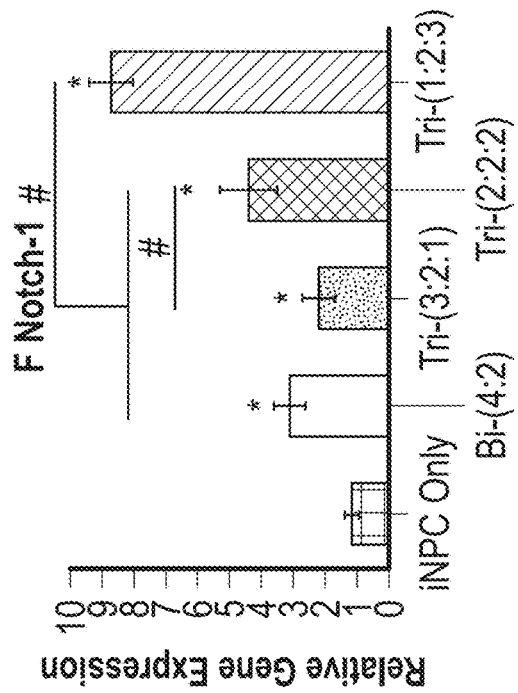
Figure 22F:
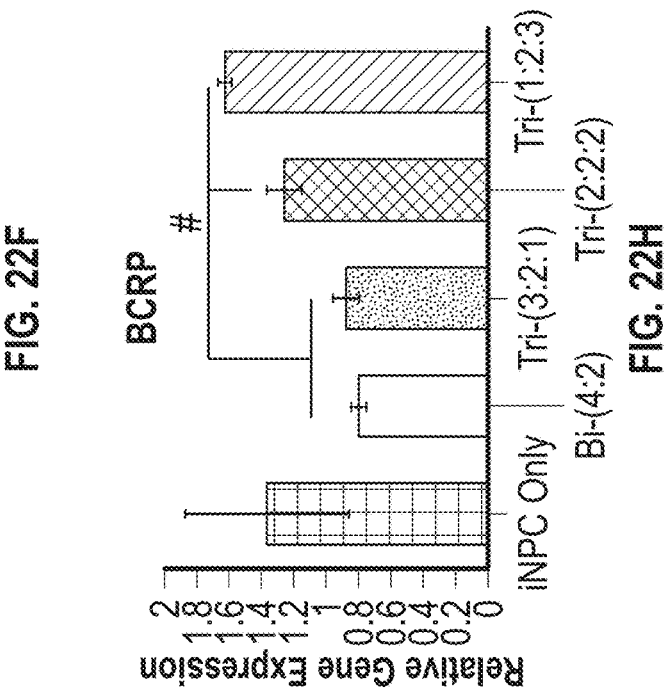
Figure 22G:
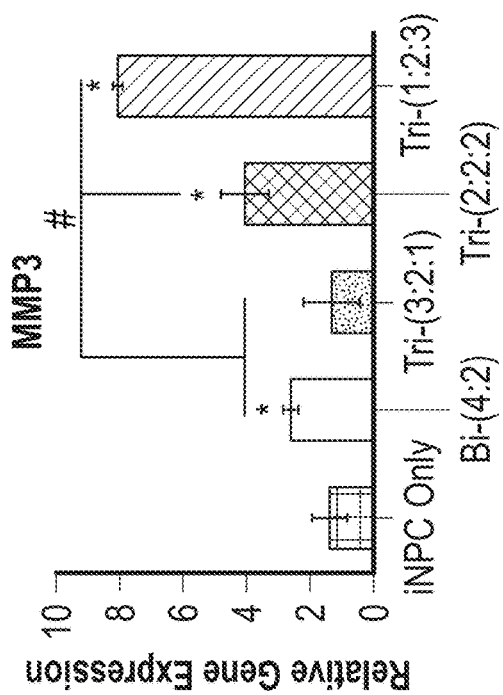
Figure 22H:
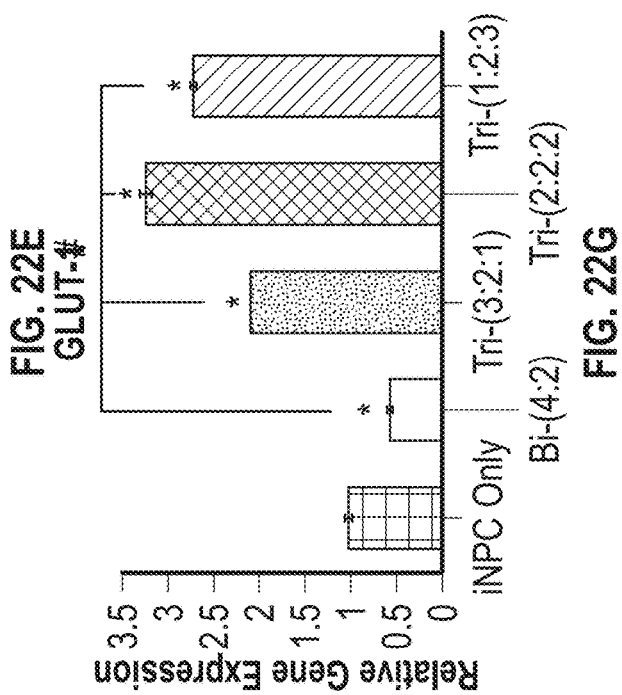

Specifically, FIGS. 22A-22I depict the results of RT-PCR analysis of gene expression of hybrid spheroids. mRNAs were isolated from day 21 hybrid spheroids for RT-PCR. Brain regional marker genes (contribution from iNPCs): TBR1 (FIG. 22A), Nkx2.1 (FIG. 22B); HOXB4 (FIG. 22C). Matrix remodeling and cell-cell communication genes (contribution from MSCs): MMP2 (FIG. 22D); MMP3 (FIG. 22E); Notch-1 (FIG. 22F). Blood-brain barrier-related genes (contributions from iECs): GLUT-1 (FIG. 22G); BCRP (FIG. 22H); PGP (FIG. 22I). *indicates p<0.05 for the test conditions compared with the iNPC only control. # indicates p<0.05 among the test conditions.

Similarly, significantly higher expression of Nkx2.1, a ventral regional marker, was observed for hybrid spheroids, i.e., 14.1±1.3, 6.7±1.4, 11.1±4.8, 50.5±1.8 fold for Bi-(4:2), Tri-(3:2:1), Tri-(2:2:2), Tri-(1:2:3) respectively than iNPC-only spheroids (FIG. 22B). However, HOXB4 was similarly expressed for all groups (FIG. 22C).

Matrix metalloproteinases (MMPs) play a critical role in neural cell proliferation, migration and differentiation [60-62]. Significantly higher expression of MMP2 was observed for hybrid spheroids than the iNPC only spheroids, i.e., 1.28±0.10, 2.02±0.13, 1.96±0.43, 3.90±0.19 fold for Bi-(4:2), Tri-(3:2:1), Tri-(2:2:2), Tri-(1:2:3) respectively (FIG. 22D). For MMP3, higher expression was observed for hybrid spheroids than iNPC only spheroids except for Tri-(3:2:1), i.e., 2.60±0.19, 1.36±0.85, 4.06±0.76, 8.05±0.09 fold for Bi-(4:2), Tri-(3:2:1), Tri-(2:2:2), Tri-(1:2:3) respectively (FIG. 22E). Notch signaling is known to enhance cell-cell communications and involved in the BBB formation. Upregulation of Notch-1 expression was observed in the hybrid spheroids, i.e., 3.10±0.48, 2.17±0.51, 4.38±0.91, 8.72±0.65 fold for Bi-(4:2), Tri-(3:2:1), Tri-(2:2:2), Tri-(1:2:3) respectively (FIG. 22F). These results suggest that incorporation of MSCs upregulated MMP2, MMP3, and Notch-1 expression.

Figure 22I:
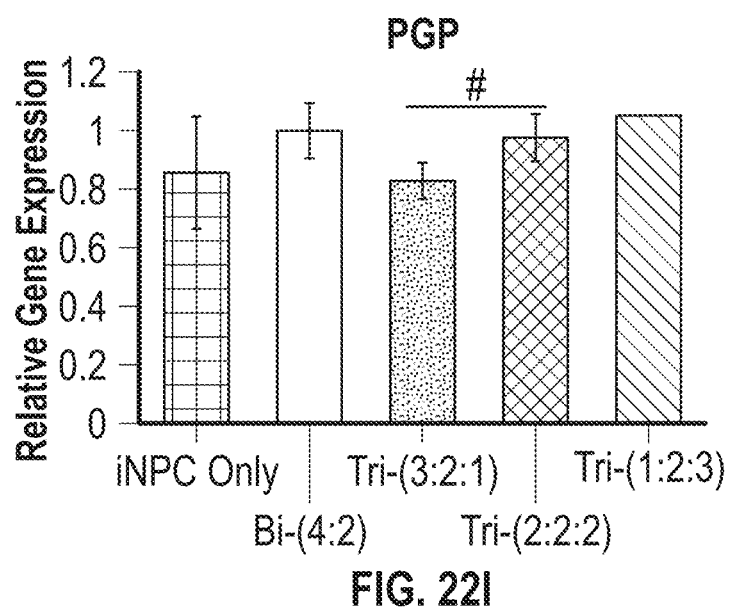

The expression of glucose transporter 1 (GLUT-1) and efflux transporters, BCRP and PGP, was determined to demonstrate whether the iECs possess BBB properties. For GLUT-1, higher expression was observed for all tri-cultured groups compared to iNPC only spheroids and Bi-(4:2) group, i.e., 0.58±0.01, 2.10±0.004, 3.23±0.07, 2.72±0.02 fold for Bi-(4:2), Tri-(3:2:1), Tri-(2:2:2), Tri-(1:2:3) respectively (FIG. 22G). BCRP was dependent on the abundance of the hMSCs, and the Tri-(1:2:3) group showed the highest BCRP gene expression, i.e., 0.80±0.03, 0.87±0.08, 1.26±0.10, 1.62±0.04 fold for Bi-(4:2), Tri-(3:2:1), Tri-(2:2:2), Tri-(1:2:3) respectively (FIG. 22H). For PGP, higher expression was observed for Tri-(2:2:2) and Tri-(1:2:3) groups compared to Tri-(3:2:1) group, i.e., 1.00±0.09, 0.83±0.06, 0.98±0.08, 1.06±0.00 fold for Bi-(4:2), Tri-(3:2:1), Tri-(2:2:2), Tri-(1:2:3) respectively (FIG. 22I). These observations indicate that co-culturing iECs with iNPCs and hMSCs increased the expression of GLUT1 and BCRP.

DNA content of hybrid spheroids was measured on merged day 1. Bi-(4:2) group showed the highest DNA content, while the DNA content in the other three groups was comparable. Specifically, FIGS. 11A-11D depict the metabolic activity and DNA content of hybrid spheroids in suspension: DNA content of hybrid neural spheroids after 1 or 7 days of tri-culture (total day 15, 21) (FIG. 11A); DNA content of hybrid spheroids with the treatment of 5% Geltrex after 7 days (total day 21) of tri-culture compared to the control (no treatment) (FIG. 11B); DNA content of hybrid spheroids with the treatment of 0.05 wt % hyaluronic acid (HA) after 7 days (total day 21) of tri-culture compared to control group (no treatment) (FIG. 11C); and MTT activity of hybrid spheroids with the treatment of 20 µM ROCKi Y27632 after 7 days (total day 21) of tri-culture compared to control group (no treatment) (FIG. 11D). *indicates p<0.05 for the different test conditions.

Figure 12:
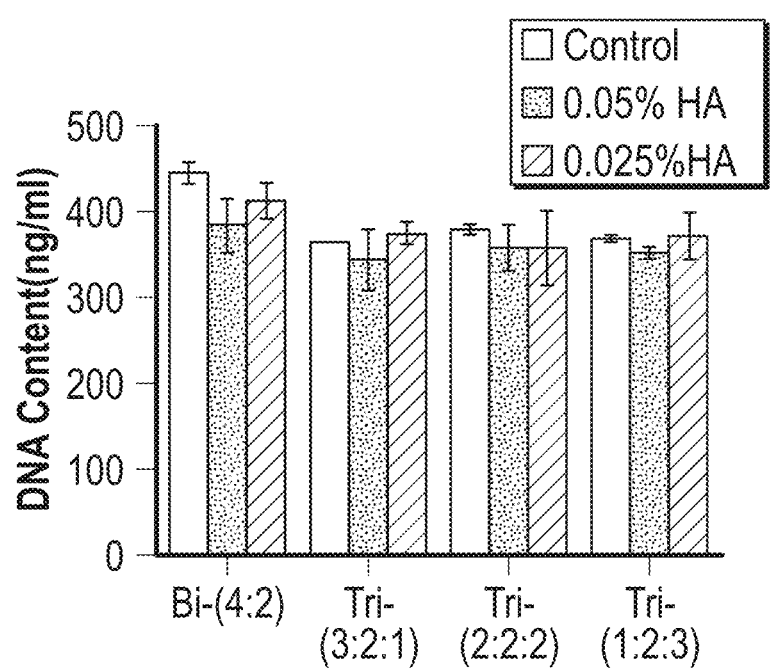
FIG. 12 depicts DNA content of hybrid spheroids with the treatment of 0.025 wt % hyaluronic acid (HA).

After 7 days of culture, all four groups showed cell proliferation with increased DNA content (FIG. 11A). Increased DNA content was observed for Tri-(2:2:2) and Tri-(1:2:3) spheroids with the treatment of 5% Geltrex (FIG. 11B). The treatment of 0.05 wt % HA showed no significant difference in DNA content except for Bi-(4:2) spheroids, while 0.025 wt % HA treatment showed no significant difference in DNA content for all the groups (FIG. 11C and FIG. 12). Higher MTT activity was observed for the Bi-(4:2) spheroids compared to the other three groups, and the treatment of ROCKi increased MTT activity (FIG. 11D). 5-Bromo-2'-deoxyuridine (BrdU) assay showed that the cells in S-phase of cell cycle were not homogeneously happening in the spheroids, but tended to be localized to the interface of the spheroids or the spheroid surface (FIG. 12). Specifically, FIG. 12 shows the DNA content of hybrid spheroids with the treatment of 0.025 wt % hyaluronic acid (HA) after 7 days (total day 21) of tri-culture compared to control group (no treatment). Confocal images of 5-Bromo-2'-deoxyuridine (BrDU), showing cells in S-phase of cell cycle were produced (not shown). For 5-Bromo-2'-deoxyuridine (BrdU) assay, the cells were incubated in medium containing 10 BrdU (Sigma) for four hours. The cells were then fixed with 70% cold ethanol, followed by a denaturation step using 2N HCl/0.5% Triton X-100 for 30 min in the dark. The samples were reduced with 1 mg/mL sodium borohydride for 5 min and incubated with mouse anti-BrdU (1:100, Life Technologies) in blocking buffer (0.5% Tween 20/1% bovine serum albumin in PBS), followed by Alexa Fluor® 488 goat anti-Mouse IgG1 (Molecular Probes). The cells were counterstained with Hoechst 33342 and analyzed by a confocal microscope (Zeiss LSM 880).

Without intending to be bound by any particular theory, it is believed that the trophic factors secreted by MSCs (e.g., FGF-2 and VEGF-A) can enhance the angiogenesis, neurogenesis, and axonal growth during neural tissue regeneration [56, 57]. MSCs also secret anti-inflammatory factors, such as TGF-β1 and PEG2, to regulate the immune response [58, 59]. The secretion levels of FGF-2, VEGF-A, PGE2, and TGF-β1 from the hybrid spheroids of Examples 2 and 3 was characterized (FIGS. 13A-13D).

Specifically, FIGS. 13A-13D depict cytokine secretion by hybrid spheroids during neural differentiation from culture supernatants collected and measured by enzyme-linked immunosorbent assay (ELISA) for different spheroids at day 21. Concentrations of FGF2 (FIG. 13A), VEGF-A (FIG. 13B), PGE2 (FIG. 13C), and TGF-β1 (FIG. 13D). iNPC only indicates day 21 iNPC spheroids; MSC only indicates day 7 MSC spheroids. *indicates p<0.05 for the test conditions compared with the iNPC only control. # indicates p<0.05 among the test conditions. $ indicates p<0.05 for the test conditions compared with the MSC only control.

Figure 13A:
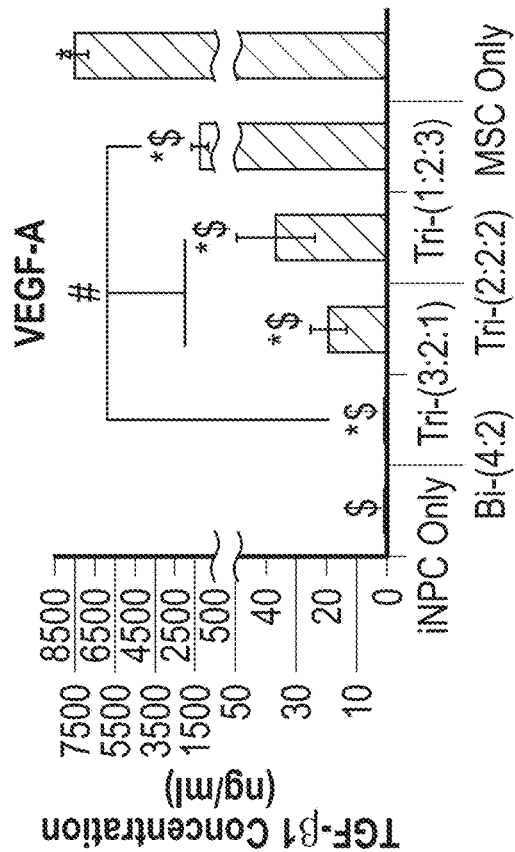
FIGS. 13A-13D depict cytokine secretion by hybrid spheroids during neural differentiation from culture supernatants collected and measured by enzyme-linked immunosorbent assay (ELISA) for different spheroids at day 21.
Figure 13B:
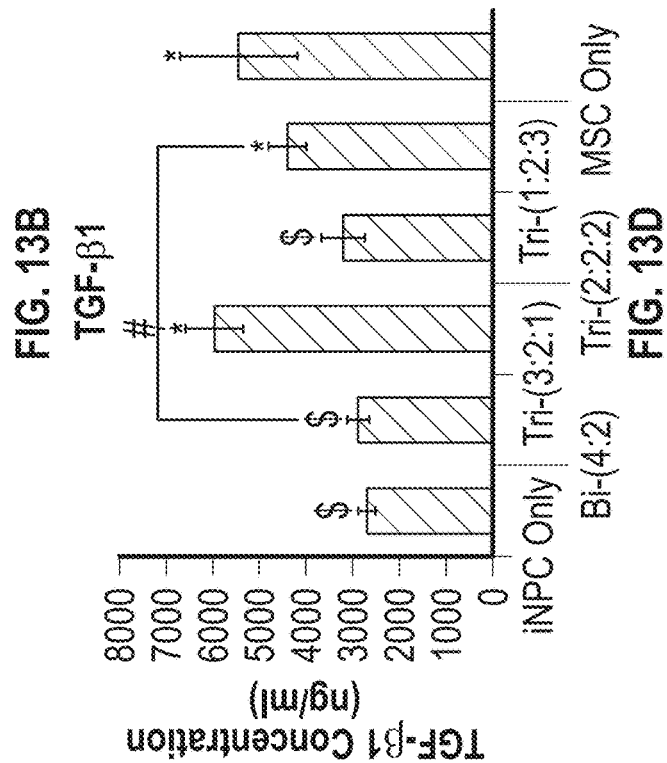
Figure 13C:
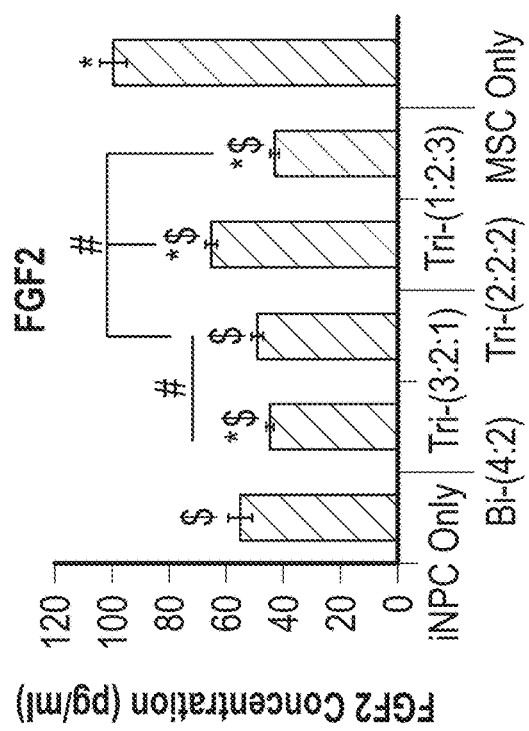
Figure 13D:
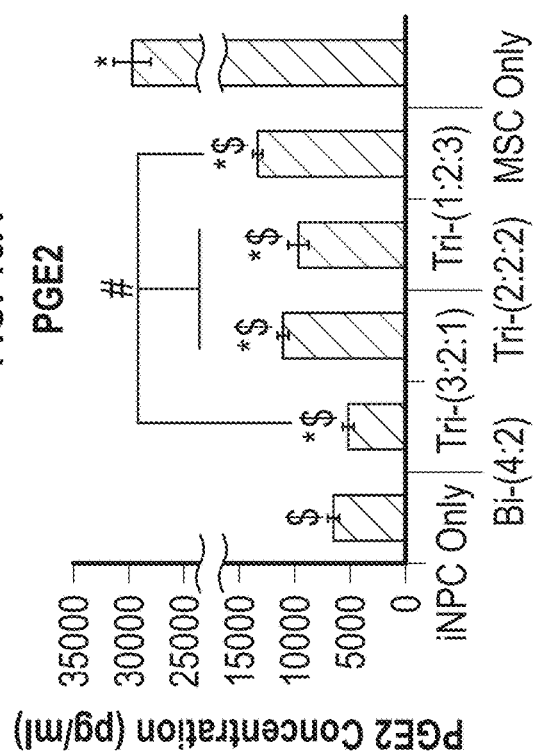
Figure 14:
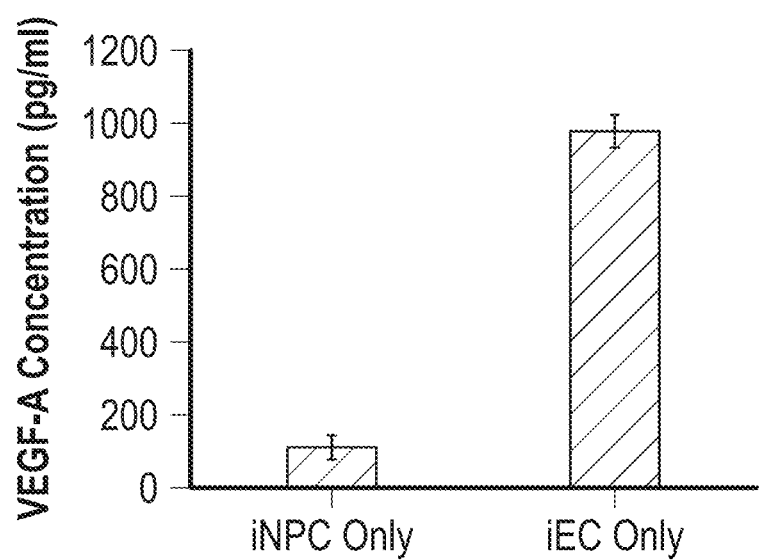
FIG. 14 depicts VEGF-A secretion of an iEC control.

The highest secretion levels were observed for the hMSC-only group. For FGF-2, higher secretion was observed for Tri-(2:2:2) spheroids compared to iNPC-only spheroids (FIG. 13A). The VEGF-A concentration increased with the relative ratio of hMSCs in the hybrid spheroids (FIG. 13B and FIG. 14). Similarly, the incorporation of hMSCs in the neural spheroids upregulated PGE2 secretion compared to iNPC-only and Bi-(4:2) groups (FIG. 13C). Tri-(3:2:1) and Tri-(1:2:3) had higher TGF-β1 concentration than the iNPC-only group (FIG. 13D). Without intending to be bound by any particular theory, it is believed that these results indicate that tri-cultures do not promote cytokine secretion, but that cytokines secretion from MSCs is maintained in hybrid spheroid culture in an amount depending on the MSC ratio used.

Effect of AMD3100

The Day 14 spheroids of Example 2 were labeled with CellTracker Red. The hMSCs were labeled with CellTracker Green. The hybrid (iNPC-iEC-MSC) spheroids were cultured in neural differentiation media (control) or media containing the CXCR4 inhibitor AMD3100 (100 nM, Sigma) for additional 10 days [53]. The fusion kinetics and cell localization were captured over time. The cell viability of day 10 hybrid spheroids was determined by MTT activity assay.

Figure 18A:
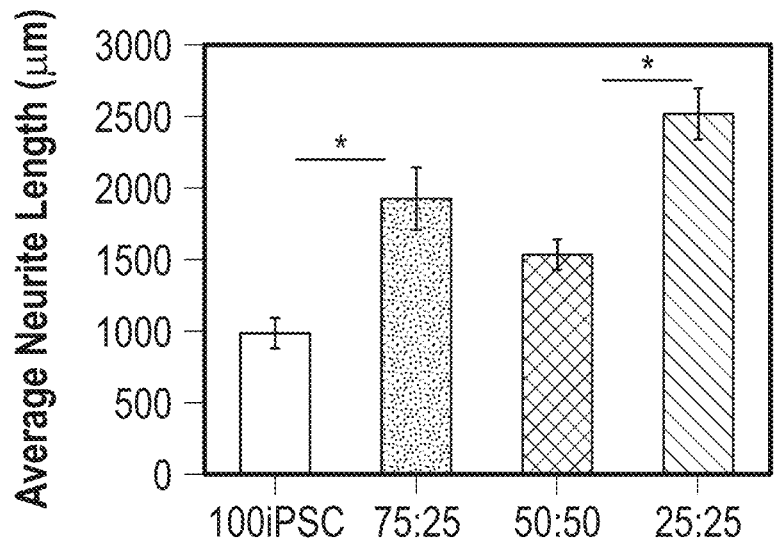
FIGS. 18A-18B depict investigation of neurogenesis of hybrid iNPC-MSC spheroids on 2D surface with iEC layer.
Figure 18B:
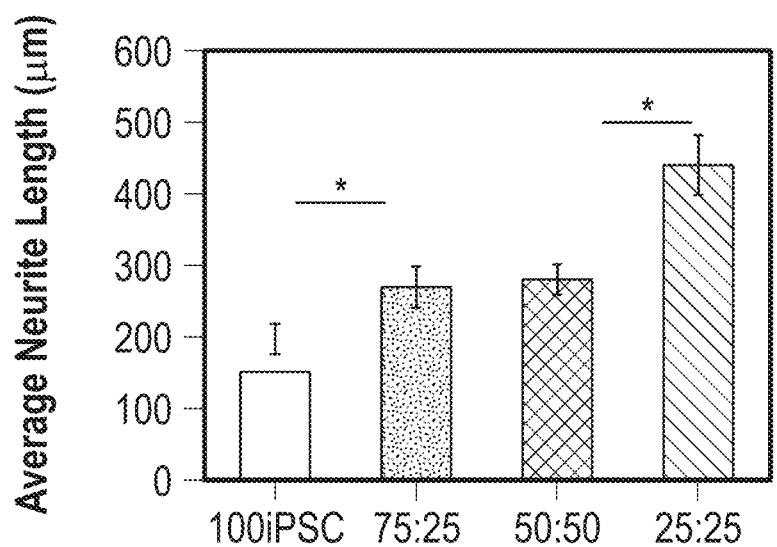

The influence of Geltrex, HA, and Y-27632 on the neurite morphology was examined (FIGS. 18A-18B). Specifically, FIGS. 18A-18B depict investigation of neurogenesis of hybrid iNPC-MSC spheroids on 2D surface with iEC layer. Day 21 hybrid iNPC-MSC spheroids were replated over per-cultured iECs for three days and immunocytochemistry was performed for neural marker β-tubulin III (not shown). Phase contrast images of axon outgrowth of day 21 hybrid iNPC-MSC spheroids replated over per-coated endothelial cells (not shown). Average neurite lengths were analyzed and shown in FIGS. 18A-18B, respectively. *indicates p<0.05 for the different test conditions.

Effects of ROCKi Y27632, Geltrex, and HA on neurogenesis of hybrid spheroids were depicted (not shown). Day 21 hybrid spheroids embedded in Geltrex (5%) or treated with ROCKi Y27632 (10 µM) were replated on 1% Geltrex-coated surface for three days. Neurite and axonal extension indicated by β-tubulin III expression was shown. Phase contrast images of axon outgrowth of day 21 spheroids were produced (not shown). Fluorescent images for day 39 spheroids: neuron marker β-tubulin III, motor neuron progenitor marker Islet-1, GABAergic neuron marker (GABA), glutamatergic neuron marker (Glutamate), cortical neuron marker (TBR1), pre-synaptic marker synapsin I and post-synaptic marker PSD95 were produced (not shown).

The neurite outgrowth was enhanced by Y27632, showing more β-tubulin III$^+$ axons and denser axons. Geltrex promoted the neurite outgrowth, but the packing density of axon was not high. Prolonged cortical differentiation was performed for day 39 hybrid spheroids treated with Geltrex or 0.025 wt % HA (not shown). The hybrid spheroids contained GABAergic neurons and Glutamatergic neurons, and expressed pre-synaptic marker synapsin I and post-synaptic marker PSD95.

Figure 23A:
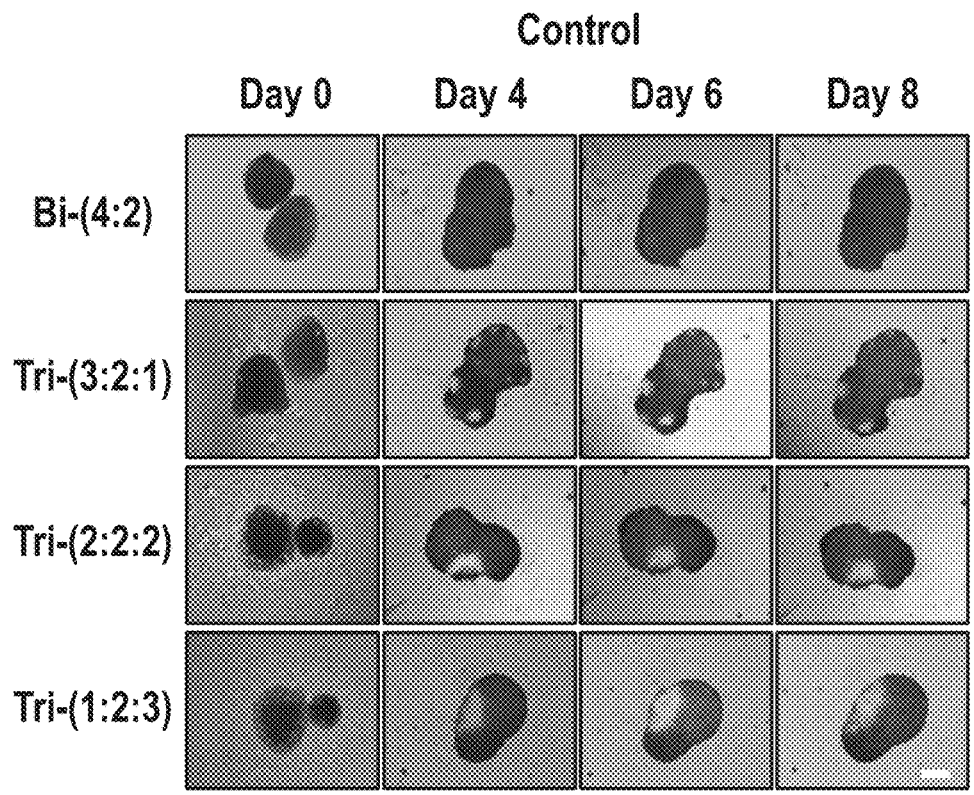
FIGS. 23A-23D depict the effects of AMD3100 treatment on the aggregation kinetics of hybrid spheroids.
Figure 23B:
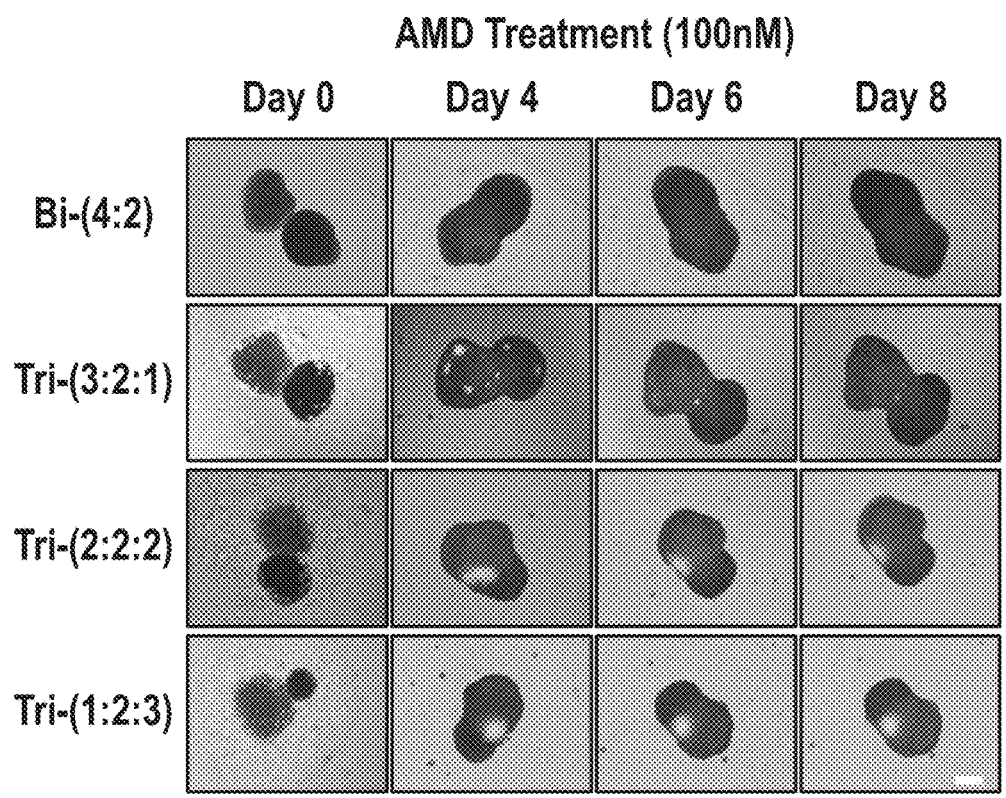

It has been reported that cell migration in cerebral organoids depends on CXCR4 (a cell homing receptor) activity [12]. To understand the spheroid fusion mechanism, the effects of CXCR4 antagonist, AMD3100, on spheroid fusion was investigated (FIGS. 23A-23D). Specifically, FIGS. 23A-23D depict the effects of AMD3100 treatment on the aggregation kinetics of hybrid spheroids. Overlay of phase contrast images (iNPCs) with fluorescent images (hMSCs labeled with CellTracker Green, iECs labeled with CellTracker Red) of different hybrid spheroids were either untreated (control) (FIG. 23A) or treated with CXCR4 inhibitor (AMD3100) (FIG. 23B). Scale bar: 400 Analysis of aspect ratios, i.e., area of MSCs in fused spheroids over total area of fused spheroid, for groups either untreated (control)

(FIG. 23C) or treated with CXCR4 inhibitor (AMD3100) (FIG. 23D). *indicates p<0.05 for the different test conditions.

Figure 19:
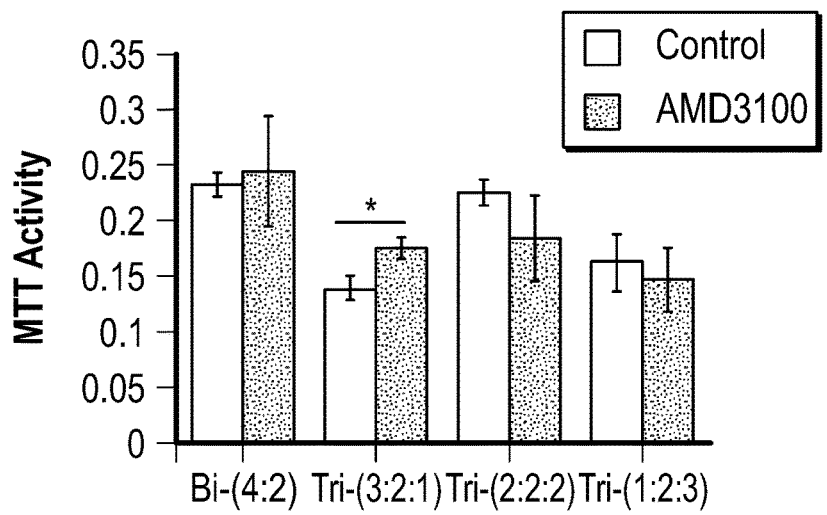
FIG. 19 depicts the effects of AMD3100 treatment on MTT activity of hybrid spheroids.
Figure 20:
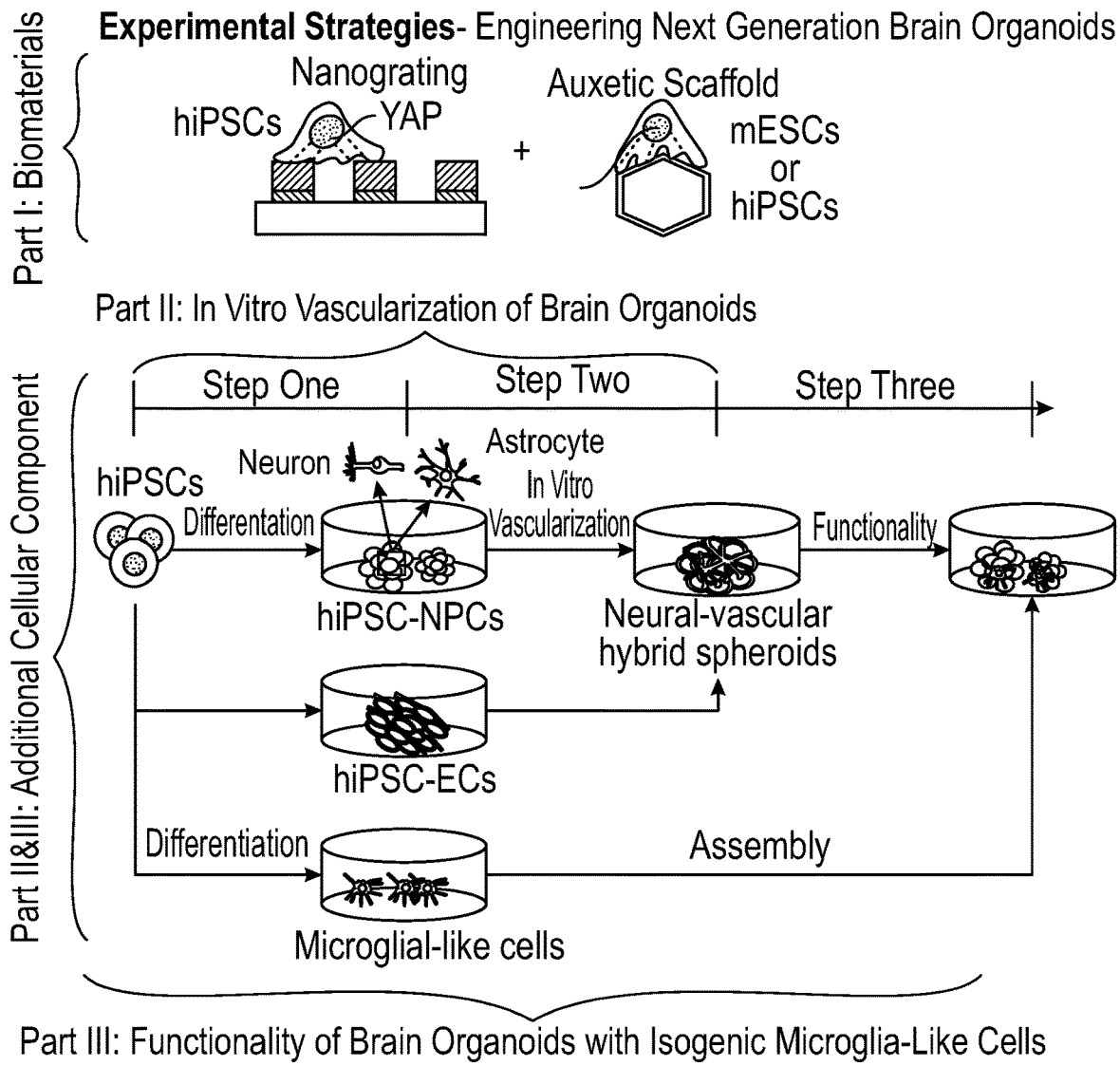
FIG. 20 depicts a schematic illustration of a process of making hybrid cortical spheroids according to an embodiment of the present disclosure.
Figure 23C:
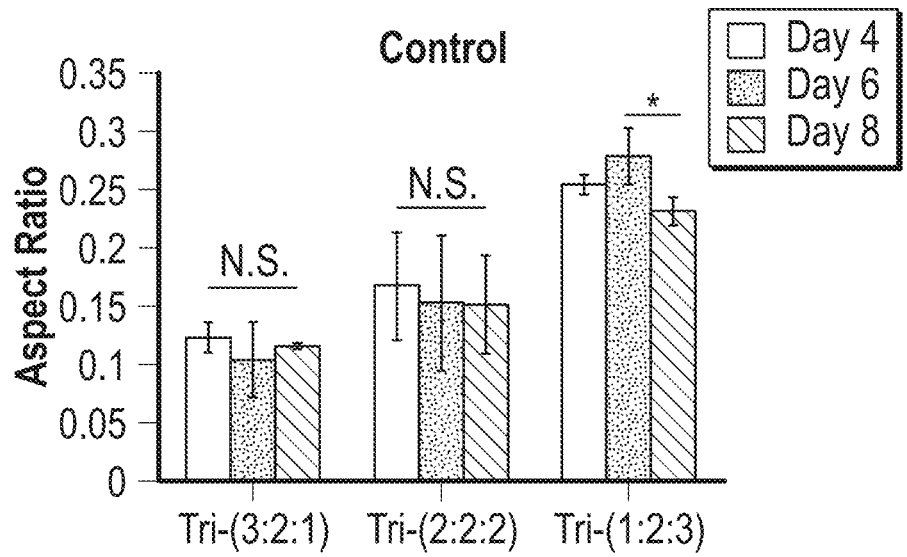
Figure 23D:
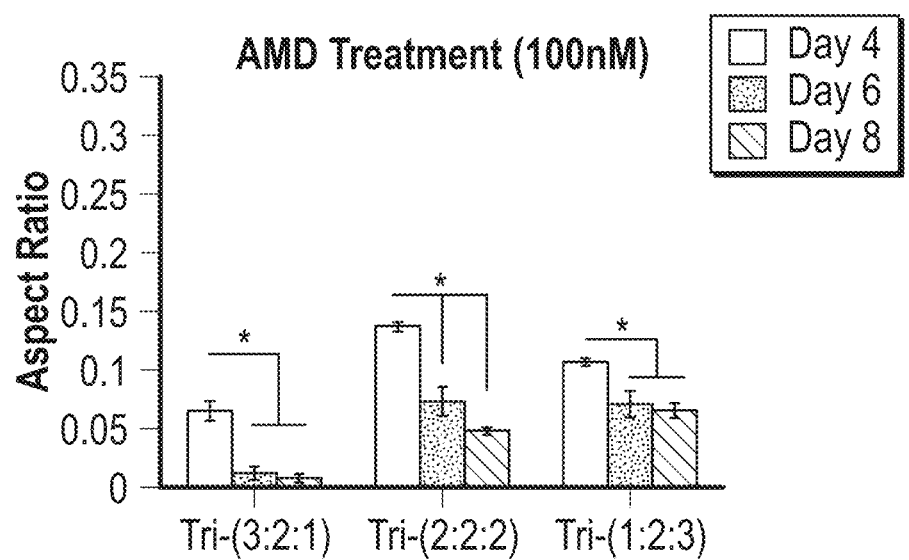

The MTT activity indicated that AMD3100 treatment had little influence on cell proliferation (FIG. 19). FIG. 19 depicts the effects of AMD3100 treatment on MTT activity of hybrid spheroids. The day 24 (after three cell types were put together) hybrid spheroids were measured for MTT activity assay after AMD3100 treatment. *indicates p<0.05 for the different test conditions.

iEC spheroids (with CellTracker Red) gradually fused with the iNPC spheroids. Small hMSC (with CellTracker Green) areas sparsely spread over the fused spheroids for Tri-(3:2:1) group. For Tri-(2:2:2) and Tri-(1:2:3) groups, one large area of hMSCs occupied the interface of iEC and iNPC spheroids (FIGS. 23A, 23C). For AMD3100 treatment, the area occupied by hMSCs was smaller than the control groups (FIGS. 23B, 23D). Analysis of the relative ratio of area occupied by hMSCs to the total area of fused spheroids showed that the aspect ratio of hMSCs decreased from day 4 to day 8 with AMD3100 treatment (FIG. 23D). Without intending to be bound by any particular theory, it is believed that these data indicate that AMD3100 may inhibit hMSC invasion during spheroid fusion.

Whole-Patch Clamping for Electrophysiology

A whole-cell patch clamp was used to record from the spheroids of Examples 2 and 3 cultured on glass covered slips. Cover slips were washed three times with extracellular recording solution containing (in mM) 136 NaCl, 4 KCl, 2 MgCl, 10 HEPES, and 1 EGTA (312 mOsm, pH 7.39) and were incubated in this solution at room temperature during recording. Glass electrodes (resistance 1-5 MΩ) were filled with intracellular solution containing 130 mM KCl, 10 mM HEPES, and 5 mM EGTA (292 mOsm, pH 7.20). Cells were visualized under phase contrast with a Nikon Eclipse Ti—U inverted microscope and attached DS-Qi1 monochrome digital camera. Recordings were made with an Axopatch 200B amplifier (Molecular Devices) and digitized with a Digidata 1440A system (Molecular Devices). Ionic currents were recorded under a voltage clamp protocol (−60 mV to 135 mV in 15 mV steps, 250 ms in duration). Action potentials were recorded under a current clamp protocol (−100 pA to 200 pA in 20 pA steps, 800 ms in duration). Spontaneous post-synaptic currents were recorded under continuous voltage clamp at −80 mV for 2 min. Signals were filtered at 1 kHz and sampled at 10 kHz. Data was collected and analyzed using pCLAMP 10 software (Molecular Devices).

The electrophysiological properties of the outgrowth cells of the derived spheroids/organoids were examined via patch clamping. As cells within the dense core of the spheroid cannot be visualized by phase contrast microscopy while in the recording chamber, outgrowth cells toward the boundary of the spheroid were chosen for these experiments. This allowed us to simultaneously evaluate the electrical activity and cellular morphology of the recorded cells for neuron-like properties. Recorded cells displayed fast inward currents and long-lasting outward currents during voltage-clamp recording, suggesting the presence of functional voltage-gated $Na^+$ and $K^+$ channels, respectively (FIGS. 16A-16D).

Figure 16A:
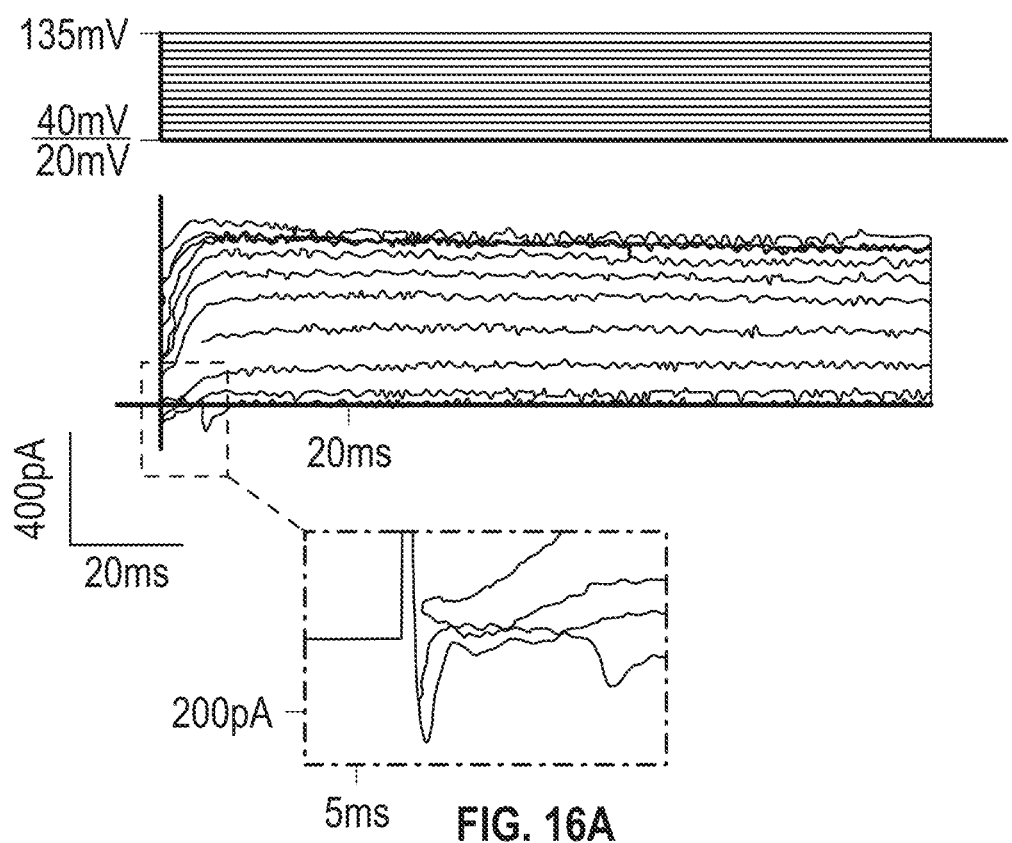
FIGS. 16A-16D depict electrophysiological properties of hybrid spheroids.
Figure 16B:
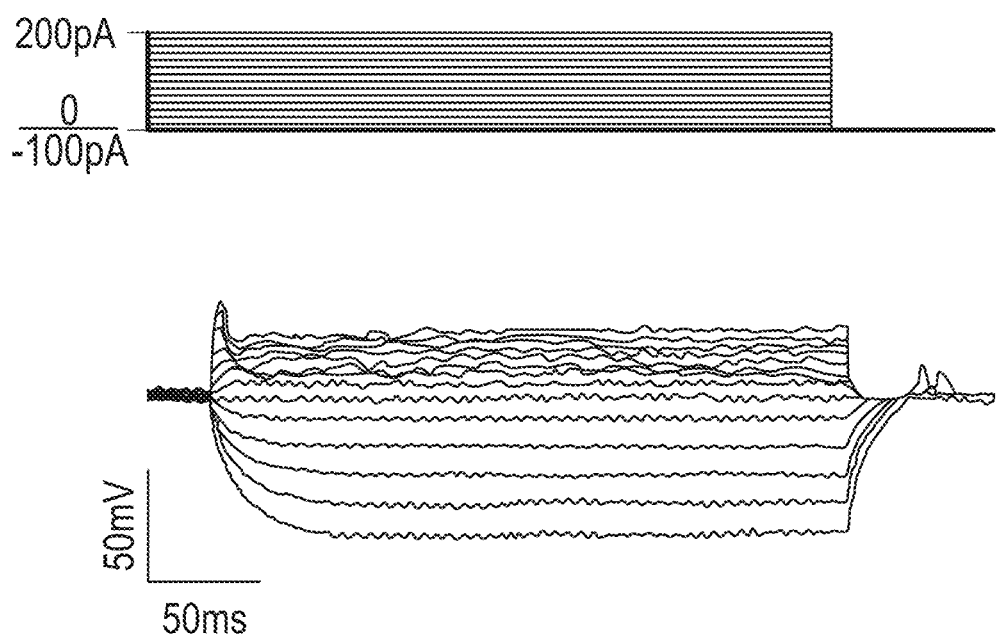
Figure 16C:
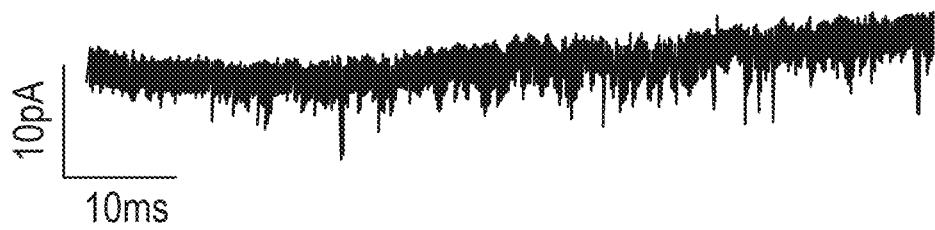
Figure 16D:
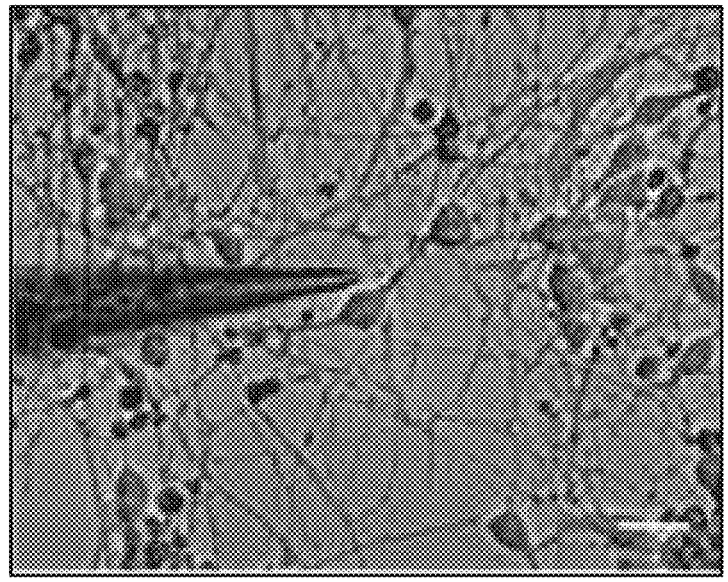

Specifically, FIGS. 16A-16D depict electrophysiological properties of hybrid spheroids (day 42). Results were from Bi-(4:2) group. Representative voltage clamp traces showing fast inward Na+ currents and long-lasting outward K+ currents evoked by depolarizing voltage steps (FIG. 16A). Step size=15 mV. Representative current clamp traces showing rebound action potentials in response to hyperpolarizing current injections (FIG. 16B). Step size=20 pA. Representative trace of continuous voltage clamp recording showing spontaneous postsynaptic currents (FIG. 16C). Representative phase-contrast images of a recorded neuron outgrowth of the spheroids (FIG. 16D). Scale bar: 20 μm.

In addition, a subpopulation of the cells fired rebound action potentials in response to hyperpolarizing current injection during current clamp recording. Spontaneous post-synaptic currents were observed in the absence of stimulation during continuous voltage clamp recording. Cellular morphology was stereotypically neuron-like, with small cell bodies and extensive long and thin projections. Together, these results suggest that the hybrid spheroids have the functional and morphological properties of neurons including synaptic activity.

While the disclosure has been described with reference to a number of embodiments, it will be understood by those skilled in the art that the invention is not limited to such disclosed embodiments. Rather, the invention can be modified to incorporate any number of variations, alterations, substitutions, or equivalent arrangements not described herein, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

REFERENCES

[1] X. Yin, et al., Engineering stem cell organoids, Cell Stem Cell, 18 (2016) 25-38.
[2] X. Qian, et al., Brain-region-specific organoids using mini-bioreactors for modeling ZIKV exposure, Cell, 165 (2016) 1238-1254.
[3] M. A. Lancaster, et al., Cerebral organoids model human brain development and microcephaly, Nature, 501 (2013) 373-379.
[4] M. A. Lancaster, J. A. Knoblich, Organogenesis in a dish: modeling development and disease using organoid technologies, Science, 345 (2014) 1247125.
[5] S. P. Pasca, The rise of three-dimensional human brain cultures, Nature, 553 (2018) 437-445.
[6] W. H. Organization, Neurological disorders affect 1 billion people: WHO, (2007).
[7] C. R. Nicholas, et al., Functional maturation of hPSC-derived forebrain interneurons requires an extended timeline and mimics human neural development, Cell Stem Cell, 12 (2013) 573-586.
[8] I. Kelava, M. A. Lancaster, Stem cell models of human brain development, Cell Stem Cell, 18 (2016) 736-748.
[9] E. Di Lullo, A. R. Kriegstein, The use of brain organoids to investigate neural development and disease, Nat Rev Neurosci, 18 (2017) 573-584.
[10] F. Birey, et al., Assembly of functionally integrated human forebrain spheroids, Nature, 545 (2017) 54-59.
[11] Y. Xiang, et al., Fusion of Regionally Specified hPSC-Derived Organoids Models Human Brain Development and Interneuron Migration, Cell Stem Cell, 21 (2017) 383-398.
[12] J. A. Bagley, et al., Fused cerebral organoids model interactions between brain regions, Nat Methods, 14 (2017) 743-751.

[13] Y. Yamazaki, T. Kanekiyo, Blood-Brain Barrier Dysfunction and the Pathogenesis of Alzheimer's Disease, Int J Mol Sci, 18 (2017) pii: E1965.

[14] S. Rafii, et al., Angiocrine functions of organ-specific endothelial cells, Nature, 529 (2016) 316-325.

[15] P. A. Fleming, et al., Fusion of uniluminal vascular spheroids: a model for assembly of blood vessels, Dev Dyn, 239 (2010) 398-406.

[16] L. Moldovan, et al., iPSC-Derived Vascular Cell Spheroids as Building Blocks for Scaffold-Free Biofabrication, Biotechnol J, (2017). doi: 10.1002/biot.201700444.

[17] D. J. Richards, et al., Inspiration from heart development: Biomimetic development of functional human cardiac organoids, Biomaterials, 142 (2017) 112-123.

[18] T. Takebe, et al., Vascularized and functional human liver from an iPSC-derived organ bud transplant, Nature, 499 (2013) 481-484.

[19] T. Takebe, et al., Vascularized and complex organ buds from diverse tissues via mesenchymal cell-driven condensation, Cell Stem Cell, 16 (2015) 556-565.

[20] A. D. Wong, et al., The blood-brain barrier: an engineering perspective, Front Neuroeng, 6 (2013) 7.

[21] A. Appelt-Menzel, et al., Establishment of a Human Blood-Brain Barrier Co-culture Model Mimicking the Neurovascular Unit Using Induced Pluri- and Multipotent Stem Cells, Stem Cell Reports, 8 (2017) 894-906.

[22] S. G. Canfield, et al., An isogenic blood-brain barrier model comprising brain endothelial cells, astrocytes, and neurons derived from human induced pluripotent stem cells, J Neurochem, 140 (2017) 874-888.

[23] K. Lauschke, et al., Paving the Way Toward Complex Blood-Brain Barrier Models Using Pluripotent Stem Cells, Stem Cells Dev, 26 (2017) 857-874.

[24] M. Ribecco-Lutkiewicz, et al., A novel human induced pluripotent stem cell blood-brain barrier model: Applicability to study antibody-triggered receptor-mediated transcytosis, Sci Rep, 8 (2018) 1873.

[25] M. Crisan, et al., A perivascular origin for mesenchymal stem cells in multiple human organs, Cell Stem Cell, 3 (2008) 301-313.

[26] L. da Silva Meirelles, et al., Mesenchymal stem cells reside in virtually all post-natal organs and tissues, J Cell Sci, 119 (2006) 2204-2213.

[27] J. Xu, et al., A systematic review: differentiation of stem cells into functional pericytes, FASEB J, 31 (2017) 1775-1786.

[28] S. Sart, et al., Three-dimensional aggregates of mesenchymal stem cells: cellular mechanisms, biological properties, and applications, Tissue Eng Part B Reviews, 20 (2014) 365-380.

[29] Q. Zhang, et al., Three-dimensional spheroid culture of human gingiva-derived mesenchymal stem cells enhances mitigation of chemotherapy-induced oral mucositis, Stem Cells Dev, 21 (2012) 937-947.

[30] L. Song, et al., Neural differentiation of spheroids derived from human induced pluripotent stem cells-mesenchymal stem cells co-culture, Tissue Eng Part A, 24 (2018) 915-929.

[31] Y. Yan, et al., Modelling neurodegenerative microenvironment using cortical organoids derived from human stem cells, Tissue Eng Part A, 24 (2018) 1125-1137.

[32] Y. Yan, et al., Derivation of cortical spheroids from human induced pluripotent stem cells in a suspension bioreactor, Tissue Eng Part A, 24 (2018) 418-431.

[33] Y. Yan, et al., Neural patterning of human induced pluripotent stem cells in 3-D cultures for studying biomolecule-directed differential cellular responses, Acta Biomater, 42 (2016) 114-126.

[34] K. Si-Tayeb, et al., Generation of human induced pluripotent stem cells by simple transient transfection of plasmid DNA encoding reprogramming factors, BMC Dev Biol, 10 (2010) 81.

[35] K. Si-Tayeb, et al., Highly efficient generation of human hepatocyte-like cells from induced pluripotent stem cells, Hepatology, 51 (2010) 297-305.

[36] Y. Yan, et al., Differential effects of acellular embryonic matrices on pluripotent stem cell expansion and neural differentiation. Biomaterials, 73 (2015) 231-242.

[37] Y. Yan, et al., Neural patterning of human induced pluripotent stem cells in 3-D cultures for studying biomolecule-directed differential cellular responses. Acta Biomater, 42 (2016) 114-126.

[38] Y. Yan, et al., Pluripotent stem cell expansion and neural differentiation in 3-D scaffolds of tunable Poisson's ratio, Acta Biomater, 49 (2017) 192-203.

[39] F. Zhao, T. Ma, Perfusion bioreactor system for human mesenchymal stem cell tissue engineering: dynamic cell seeding and construct development, Biotechnol Bioeng, 91 (2005) 482-493.

[40] W. L. Grayson, et al., Human mesenchymal stem cells tissue development in 3D PET matrices, Biotechnol Prog, 20 (2004) 905-912.

[41] N. Munoz, et al., Gas chromatography-mass spectrometry analysis of human mesenchymal stem cell metabolism during proliferation and osteogenic differentiation under different oxygen tensions, J Biotechnol, 169 (2014) 95-102.

[42] W. L. Grayson, et al., Effects of hypoxia on human mesenchymal stem cell expansion and plasticity in 3D constructs, J Cell Physiol, 207 (2006) 331-339.

[43] X. Lian, et al., Efficient differentiation of human pluripotent stem cells to endothelial progenitors via small-molecule activation of WNT signaling, Stem Cell Reports, 3 (2014) 804-816.

[44] T. Qian, et al., Directed differentiation of human pluripotent stem cells to blood-brain barrier endothelial cells, Sci Adv, 3 (2017) e1701679.

[45] R. Olmer, et al., Differentiation of Human Pluripotent Stem Cells into Functional Endothelial Cells in Scalable Suspension Culture, Stem Cell Reports, 10 (2018) 1657-1672.

[46] B. C. Gettler, et al., Formation of Adipose Stromal Vascular Fraction Cell-Laden Spheroids Using a Three-Dimensional Bioprinter and Superhydrophobic Surfaces, Tissue Eng Part C Methods, 23 (2017) 516-524.

[47] A. C. Tsai, et al., Compaction, fusion, and functional activation of three-dimensional human mesenchymal stem cell aggregate, Tissue Eng Part A, 21 (2015) 1705-1719.

[48] Y. Liu, et al., Metabolic Reconfiguration Supports Reacquisition of Primitive Phenotype in Human Mesenchymal Stem Cell Aggregates, Stem Cells, 35 (2017) 398-410.

[49] K. Gwon, et al., Heparin-hyaluronic acid hydrogel in support of cellular activities of 3D encapsulated adipose derived stem cells, Acta Biomater, 49 (2017) 284-295.

[50] S. Sart, et al. Extracellular matrices decellularized from embryonic stem cells maintained their structure and signaling specificity, Tissue Eng Part A 20 (2014) 54-66.

[51] L. Song, et al., PCL-PDMS-PCL copolymer-based microspheres mediate cardiovascular differentiation from embryonic stem cells, Tissue Eng Part C: Methods. 23 (2017) 627-640.

[52] L. Song, et al., Nanotopography promoted neuronal differentiation of human induced pluripotent stem cells, Colloids Surf B: Biointerfaces, 148 (2016) 49-58.

[53] A. F. Cashen, et al., AMD3100: CXCR4 antagonist and rapid stem cell-mobilizing agent, Future Oncol, 3 (2007) 19-27.

[54] M. A. Lancaster, et al., Guided self-organization and cortical plate formation in human brain organoids, Nat Biotechnol, 35 (2017) 659-666.

[55] L. W. Lau, et al., Pathophysiology of the brain extracellular matrix: a new target for remyelination, Nat Rev Neurosci, 14 (2013) 722-729.

[56] R. Soares, et al., 17β-Estradiol-mediated vessel assembly and stabilization in tumor angiogenesis requires TGFβ and EGFR crosstalk, Angiogenesis, 6 (2003) 271-281.

[57] J. A. Park, et al., Coordinated interaction of the vascular and nervous systems: from molecule-to cell-based approaches, Biochemical and biophysical research communications, 311 (2003) 247-253.

[58] S. M. Park, et al., Transforming growth factor-beta1 regulates the fate of cultured spinal cord-derived neural progenitor cells, Cell Prolif, 41 (2008) 248-264.

[59] P. Kalinski, Regulation of immune responses by prostaglandin E2, The Journal of Immunology, 188 (2012) 21-28.

[60] G. A. Tonti, et al., Neural stem cells at the crossroads: MMPs may tell the way, Int J Dev Biol, 53 (2003) 1-17.

[61] B. Z. Barkho, et al., Endogenous Matrix Metalloproteinase (MMP)-3 and MMP-9 Promote the Differentiation and Migration of Adult Neural Progenitor Cells in Response to Chemokines, Stem Cells, 26 (2008) 3139-3149.

[62] C. M. Madl, et al., Maintenance of neural progenitor cell stemness in 3D hydrogels requires matrix remodelling, Nat Mater, 16 (2017) 1233-1242.

[63] M. Bershteyn, et al., Human iPSC-Derived Cerebral Organoids Model Cellular Features of Lissencephaly and Reveal Prolonged Mitosis of Outer Radial Glia, Cell Stem Cell, 20 (2017) 435-449 e434.

[64] M. P. Schwartz, et al., Human pluripotent stem cell-derived neural constructs for predicting neural toxicity, Proc Natl Acad Sci USA, 112 (2015) 12516-12521.

[65] Y. Sasai, Next-generation regenerative medicine: organogenesis from stem cells in 3D culture, Cell Stem Cell, 12 (2013) 520-530.

[66] Y. Sasai, Cytosystems dynamics in self-organization of tissue architecture, Nature, 493 (2013) 318-326.

[67] A. Lowe, et al., Intercellular Adhesion-Dependent Cell Survival and ROCK-Regulated Actomyo sin-Driven Forces Mediate Self-Formation of a Retinal Organoid, Stem Cell Reports, 6 (2016) 743-756.

[68] M. Campisi, et al., 3D self-organized microvascular model of the human blood-brain barrier with endothelial cells, pericytes and astrocytes, Biomaterials, 180 (2018) 117-129.

[69] L. M. Acevedo, et al., hESC Differentiation toward an Autonomic Neuronal Cell Fate Depends on Distinct Cues from the Co-Patterning Vasculature, Stem Cell Reports, 4 (2015) 1075-1088.

[70] S. Ishii, et al., Stromal cell-secreted factors promote the survival of embryonic stem cell-derived early neural stem/progenitor cells via the activation of MAPK and PI3K-Akt pathways, J Neurosci Res, 88 (2010) 722-734.

[71] Y. Wang, et al., Mesenchymal stem cells regulate the proliferation and differentiation of neural stem cells through Notch signaling, Cell Biol Int, 33 (2009) 1173-1179.

[72] H. W. Han, S. H. Hsu, Chitosan derived co-spheroids of neural stem cells and mesenchymal stem cells for neural regeneration, Colloids Surf B Biointerfaces, 158 (2017) 527-538.

[73] Q. Shen, et al., Endothelial cells stimulate self-renewal and expand neurogenesis of neural stem cells, Science, 304 (2004) 1338-1340.

[74] A. P. Robinson, et al., Human stem/progenitor cells from bone marrow enhance glial differentiation of rat neural stem cells: a role for transforming growth factor beta and Notch signaling, Stem Cells Dev, 20 (2011) 289-300.

[75] J. M. Santos, et al., Three-dimensional spheroid cell culture of umbilical cord tissue-derived mesenchymal stromal cells leads to enhanced paracrine induction of wound healing, Stem Cell Res Ther, 6 (2015) 90.

[76] M. M. Valente, et al., The MMP-1/PAR-1 axis enhances proliferation and neuronal differentiation of adult hippocampal neural progenitor cells, Neural Plasticity, 2015 (2015).

[77] R. M. Brick, et al., Neurotrophically Induced Mesenchymal Progenitor Cells Derived from Induced Pluripotent Stem Cells Enhance Neuritogenesis via Neurotrophin and Cytokine Production, Stem Cells Transl Med, 7 (2017) 45-58.

[78] K.-W. Wu, et al., Neurovascular Interaction Promotes the Morphological and Functional Maturation of Cortical Neurons, Front Cell Neurosci, 11 (2017) 290.

[79] Q. Li, et al., Modeling the neurovascular niche: VEGF- and BDNF-mediated cross-talk between neural stem cells and endothelial cells: an in vitro study, J Neurosci Res, 84 (2006) 1656-1668.

[80] L. Cao, et al., Promoting angiogenesis via manipulation of VEGF responsiveness with notch signaling, Biomaterials, 30 (2009) 4085-4093.

[81] C. H. Chou, M. Modo, Human neural stem cell-induced endothelial morphogenesis requires autocrine/paracrine and juxtacrine signaling, Sci Rep, 6 (2016) 29029.

[82] J. M. Kelm, et al., 3D microtissue formation of undifferentiated bone marrow mesenchymal stem cells leads to elevated apoptosis, Tissue Eng Part A, 18 (2011) 692-702.

[83] W. X. Gao, et al., Effects of mesenchymal stem cells from human induced pluripotent stem cells on differentiation, maturation, and function of dendritic cells, Stem Cell Res Ther, 8 (2017) 48.

[84] A. A. Mansour, et al., An in vivo model of functional and vascularized human brain organoids, Nat Biotechnol, 36 (2018) 432-441.

[85] M. T. Pham, et al., Generation of human vascularized brain organoids, Neuroreport, 29 (2018) 588-593.

That which is claimed is:

1. A method of making a hybrid neurovascular spheroid comprising:
    propagating cortical cells to form a cortical spheroid;
    propagating endothelial cells to form an endothelial spheroid;
    propagating mesenchymal stem cells to form a mesenchymal cell culture; and
    combining the cortical spheroid, endothelial spheroid, and mesenchymal spheroid under conditions to form the hybrid neurovascular spheroid.

2. The method of claim 1, wherein the step of combining the cortical spheroid, endothelial spheroid, and mesenchymal spheroid under conditions to form a fused spheroid comprises:
    a) combining at least a portion of the mesenchymal cell culture with the cortical spheroid to form a mesenchymal cell-cortical spheroid; and
    b) combining the mesenchymal cell-cortical spheroid with the endothelial spheroid to form the hybrid neurovascular spheroid.

3. The method of claim 1, wherein the step of combining the cortical spheroid, endothelial spheroid, and mesenchymal spheroid under conditions to form a fused spheroid comprises:
    a) combining at least a portion of the mesenchymal cell culture with the endothelial spheroid to form a mesenchymal cell-endothelial spheroid; and
    b) combining the mesenchymal cell-endothelial spheroid with the cortical spheroid to form the hybrid neurovascular spheroid.

4. The method of claim 1, wherein the cortical cells are human induced pluripotent stem cells (iPSC)-derived cortical neural progenitor cells (iNPC).

5. The method of claim 4, wherein the cortical cells are pericytes, astrocytes, or microglia.

6. The method of claim 1, wherein the endothelial cells are human endothelial cells (iEC).

7. The method of claim 1, wherein the mesenchymal stem cells are human mensenchymal stem cells (hMSC).

8. The method of claim 1, wherein the ratio based on initial seeded cell numbers of the cortical cells to the endothelial cells to the mesenchymal stem cells is from about 4:2:0 to about 1:2:3.

9. The method of claim 1, wherein the cortical cells, endothelial cells, and mesenchymal stem cells are propagated in separate low-attachment well plates.

10. The method of claim 1, wherein one or more of the cortical cells, endothelial cells, and mesenchymal stem cells are propagated in a hydrogel comprising basement membrane, hyaluronic acid, or any combination thereof.

11. The method of claim 10, wherein the one or more cortical cells, endothelial cells, and mesenchymal stem cells are propagated in a hydrogel comprising at least about 5 wt. % basement membrane and 0.025 wt. % HA.

12. The method of claim 1, further comprising treating one or more of the spheroids with a CXCR4 antagonist.

13. The method of claim 12, wherein the CXCR4 antagonist is AMD3100.

* * * * *

SEQUENCE LISTING

<160> NUMBER OF SEQ ID NOS: 20

<210> SEQ ID NO 1
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccccctcgtc tttctcttac c                                                    21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aattccttct ccagctccaa ga                                                   22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagtccagag ccatgtcagc                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catcgctcag atccgtggtg                                                      20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccatctcttc cttcaggcgt                                                      20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cactgctgcc ctccccgttc                                                      20

<210> SEQ ID NO 7
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
agcaactgtg tggtccctac g                                            21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggtgtgcg tcagaatcat c                                            21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accactctcc cacctccctt a                                            21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtactccgtg tggatcggcg                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taatgtggag gccgagactt g                                            21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctggatgcg caaagttca                                               19

<210> SEQ ID NO 13
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 13
gcataaaaca gctttggggt gt                                              22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcatcaatct tttccgggag c                                               21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgcctcttg ggtatccagc                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttcaggtgcc cgatgcccag                                                 20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaggtccggc ctttagtctc a                                               21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tccaggagtg gtcagattcc tt                                              22

<210> SEQ ID NO 19
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 19
tttagctggg ctgcgtttac a                                              21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aagcatttgc ggtggacgat gg                                             22
```